(12) United States Patent
Wasinger et al.

(10) Patent No.: US 9,797,912 B2
(45) Date of Patent: Oct. 24, 2017

(54) DIAGNOSTIC METHOD FOR INFLAMMATORY BOWEL DISEASE

(71) Applicants: NEWSOUTH INNOVATIONS PTY LIMITED, New South Wales (AU); SYDNEY LOCAL HEALTH DISTRICT, Camperdown, New South Wales (AU)

(72) Inventors: Valerie Christine Wasinger, Lugarno (AU); Rupert Wing-Loong Leong, Glebe (AU)

(73) Assignee: NEWSOUTH INNOVATIONS PTY LIMITED, New South Wales (AU)

( * ) Notice: Subject to any disclaimer, the term of this patent is extended or adjusted under 35 U.S.C. 154(b) by 0 days.

(21) Appl. No.: 14/900,867

(22) PCT Filed: Jun. 27, 2014

(86) PCT No.: PCT/AU2014/000682
§ 371 (c)(1),
(2) Date: Dec. 22, 2015

(87) PCT Pub. No.: WO2014/205507
PCT Pub. Date: Dec. 31, 2014

(65) Prior Publication Data
US 2016/0161503 A1 Jun. 9, 2016

(30) Foreign Application Priority Data
Jun. 28, 2013 (AU) .................... 2013902409

(51) Int. Cl.
*G01N 33/68* (2006.01)

(52) U.S. Cl.
CPC ..... *G01N 33/6893* (2013.01); *G01N 2560/00* (2013.01); *G01N 2800/065* (2013.01)

(58) Field of Classification Search
CPC ...... C07K 7/08; C07K 14/47; C07K 14/4705; G01N 33/68; G01N 33/6893; G01N 2560/00; G01N 2800/065
See application file for complete search history.

(56) References Cited

U.S. PATENT DOCUMENTS

| 2003/0022208 A1* | 1/2003 | Lindquist | C07K 14/47 435/6.16 |
| 2009/0258848 A1 | 10/2009 | Chakravarti et al. | |
| 2010/0183719 A1* | 7/2010 | Murray | A61K 38/1841 424/484 |
| 2012/0237962 A1* | 9/2012 | Kas | G01N 33/68 435/23 |

FOREIGN PATENT DOCUMENTS

| WO | WO 2001/029269 | 4/2001 |
| WO | WO 2004/097424 A1 * | 11/2004 |
| WO | WO 2008/021290 | 2/2008 |

OTHER PUBLICATIONS

International Search Report issued by the International Searching Authority dated Sep. 16, 2014 for international application PCT/AU2014/000682, filed on Jun. 27, 2014 and published as WO 2014/205507 dated Dec. 31, 2014 (Applicant—NewSouth Innovations PTY Limited, et al. // Inventor—Valerie C. Wasinger, et al.) (7 pages).
Derici, U. et al. "Does the urinary excretion of a1-microglobulin and albumin predict clinical disease activity in ulcerative colitis?", Advances in Therapy, 2008, vol. 25, pp. 1342-1352.
Han, N.Y. et al., "Quantitative proteomic approaches in biomarker discovery of inflammatory bowel disease?", Journal of Digestive Diseases, 2012, vol. 13, pp. 497-503.
M'Koma, A.E. et al., "Proteomic profiling of mucosal and submucosal colonic tissues yields protein signatures that differentiate the inflammatory colitides", Inflammatory Bowel Disease, 2011, vol. 17, pp. 875-883.
Strid, H. et al. "Fecal chromogranins and secretogranins are increased in patients with ulcerative colitis but are not associated with disease activity", Journal of Crohn's and Colitis, 2013, vol. 7, e615-e622.
Anderson and Hunter, "Quantitative Mass Spectrometric Multiple Reaction Monitoring Assays for Major Plasma Proteins," (2006) MCP, 5(4): pp. 573-589.
Baumgart and Sandborn, "Inflammatory bowel disease: clinical aspects and established and evolving therapies," The Lancet 369 (2007) 1641-1657.
Echan, et al., "Depletion of multiple high-abundance proteins improves protein profiling capacities of human serum and plasma," (2005) Proteomics 5: pp. 3292-3303.
Gatlin, et al., "Protein Identification at the Low Femtomole Level from Silver-Stained Gels Using a New Fritless Electrospray Interface for Liquid Chromatography—Microspray and Nanospray Mass Spectrometry,"(1998) Anal. Biochem. 263(1): 93-101.
Ly and Wasinger, "Peptide enrichment and protein fractionation using selective electrophoresis," (2008) Proteomics 8(20): pp. 4197-4208.
Omenn, "Overview of the HUPO Plasma Proteome Project: Results from the pilot phase with 35 collaborating laboratories and multiple analytical groups, generating a core dataset of 3020 proteins and a publicly-available database," (2005) Proteomics 5: pp. 3226-3245.

* cited by examiner

*Primary Examiner* — Jeffrey E Russel
(74) *Attorney, Agent, or Firm* — Ballard Spahr LLP

(57) ABSTRACT

The invention relates to a method of diagnosing or assessing an inflammatory bowel disease in a subject, comprising comparing the level of one or more markers in a tissue or body fluid of the subject relative to a reference value for the one or more markers, wherein the marker is selected from the group consisting of Secretogranin-1 or a fragment thereof, guanylin or a fragment thereof, SPP 24 or a fragment thereof, AMBP or a fragment thereof; and serglycin or a fragment thereof.

11 Claims, 16 Drawing Sheets

Figure 1

A. HUMAN Secretogranin-1
MQPTLLLSLLGAVGLAAVNSMPVDNRNHNEGMVTRCIIEVLSNALSKSSAPPITPECRQV
LKTSRKDVKDKETTENENTKFEVRLLRDPADASEAHESSSRGEAGAPGEEDIQGPTKADT
EKWAEGGGHSRERADEPQWSLYPSDSQVSEEVKTRHSEKSQREDEEEEGENYQKGERGE
DSSEEKHLEEPGETQNAFLNERKQASAIKKEELVARSETHAAGHSQEKTHSREKSSQESG
EETGSQENHPQESKGQPRSQEESEEGEEDATSEVDKRRTRPRHHHGRSRPDRSSQGGSLP
SEEKGHPQEESEESNVSMASLGEKRDHHSTHYRASEEEPEYGEEIKGYPGVQAPEDLEWE
RYRGRGSEEYRAPRPQSEESWDEEDKRNYPSLELDKMAHGYGEESEEERGLEPGKGRHHR
GRGGEPRAYFMSDTREEKRFLGEGHHRVQENQMDKARRHPQGAWKELDRNYLNYGEEGAP
GKWQQQGDLQDTKENREEARFQDKQYSSHHTAEKRKRLGELFNPYYDPLQWKSSHFERRD
NMNDNFLEGEEENELTLNEKNFFPEYNYDWWEKKPFSEDVNWGYEKRNLARVPKLDLKRQ
YDRVAQLDQLLHYRKKSAEFPDFYDSEEPVSTHQEAENEKDRADQTVLTEDEKKELENLA
AMDLELQKIAEKFSQRG (SEQ ID NO: 1)

B. HUMAN Guanylin
MNAFLLSALCLLGAWAALAGGVTVQDGNFSFSLESVKKLKDLQEPQEPRVGKLRNFAPIP
GEPVVPILCSNPNFPEELKPLCKEPNAQEILQRLEEIAEDPGTCEICAYAACTGC(SEQ ID NO: 3)

C. HUMAN Secreted phosphoprotein 24 (SPP24)
MISRMEKMTMMMKILIMFALGMNYWSCSGFPVYDYDPSSLRDALSASVVK**VNSQSLSPYL
FR**AFRSSLKRVEVLDENNLVMNLEFSIRETTCRKDSGEDPATCAFQRDYYVSTAVCRSTV
KVSAQQVQGVHARCSWSSSTSESYSSEEMIFGDMLGSHKWRNNYLFGLISDESISEQFYD
RSLGIMRRVLPPGNRRYPNHRHRARINTDFE (SEQ ID NO: 5)

D. HUMAN Serglycin
MMQKLLKCSRLVLALALILVLESSVQGYPTRRARYQWVRCNPDSNSANCLEEKGPMFELL
PGESNKIPRLRTDLFPKTRIQDLNRIFPLSEDYSGSGFGSGSGSGSGSGSGFLTEMEQDY
QLVDESDAFHDNLRSLDRNLPSDSQDLGQHGLEEDFML(SEQ ID NO: 8)

E. HUMAN Protein AMBP
MRSLGALLLLLSACLAVSAGPVPTPPDNIQVQENFNISRIYGKWYNLAIGSTCPWLKKIM
DRMTVSTLVLGEGATEAEISMTSTRWRKGVCEETSGAYEKTDTDGKFLYHKSKWNITMES
YVVHTNYDEYAIFLTKKFSRHHGPTITAKLYGRAPQLRETLLQDFRVVAQGVGIPEDSIF
TMADRGECVPGEQEPEPILIPRVRRAVLPQEEEGSGGGQLVTEVTKKEDSCQLGYSAGPC
MGMTSRYFYNGTSMACETFQYGGCMGNGNNFVTEKECLQTCRTVAACNLPIVRGPCRAFI
QLWAFDAVKGKCVLFPYGGCQGNGNKFYSEKECREYCGVPGDGDEELLRFSN (SEQ ID NO: 10)

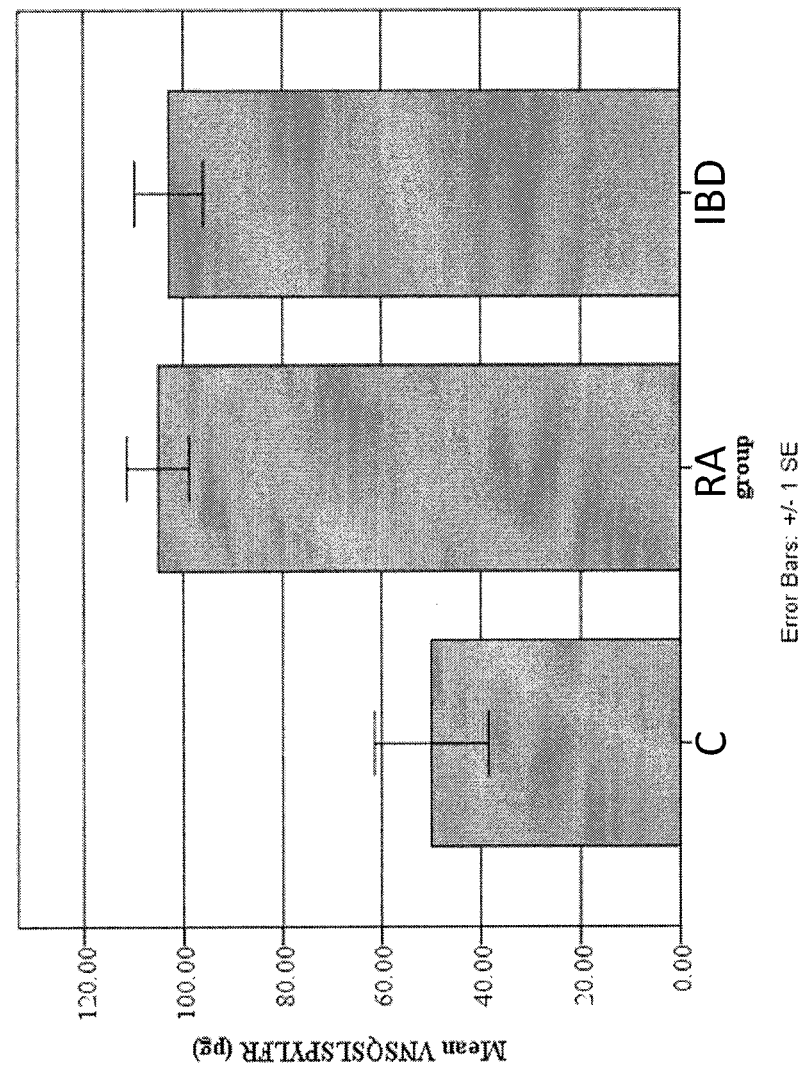

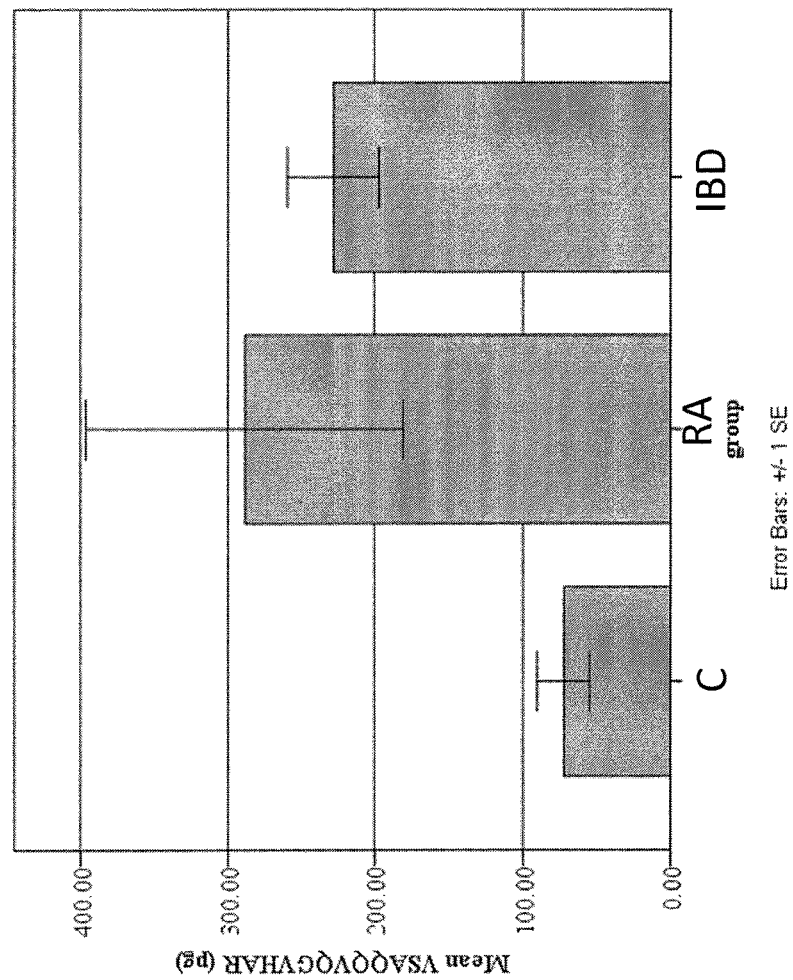

SEQUENCE LISTING

```
<160> NUMBER OF SEQ ID NOS: 12

<210> SEQ ID NO 1
<211> LENGTH: 677
<212> TYPE: PRT
<213> ORGANISM: Homo sapiens

<400> SEQUENCE: 1

Met Gln Pro Thr Leu Leu Leu Ser Leu Leu Gly Ala Val Gly Leu Ala
1               5                   10                  15

Ala Val Asn Ser Met Pro Val Asp Asn Arg Asn His Asn Glu Gly Met
            20                  25                  30

Val Thr Arg Cys Ile Ile Glu Val Leu Ser Asn Ala Leu Ser Lys Ser
        35                  40                  45

Ser Ala Pro Pro Ile Thr Pro Glu Cys Arg Gln Val Leu Lys Thr Ser
    50                  55                  60

Arg Lys Asp Val Lys Asp Lys Glu Thr Thr Glu Asn Glu Asn Thr Lys
65                  70                  75                  80

Phe Glu Val Arg Leu Leu Arg Asp Pro Ala Asp Ala Ser Glu Ala His
                85                  90                  95

Glu Ser Ser Ser Arg Gly Glu Ala Gly Ala Pro Gly Glu Glu Asp Ile
            100                 105                 110

Gln Gly Pro Thr Lys Ala Asp Thr Glu Lys Trp Ala Glu Gly Gly Gly
        115                 120                 125

His Ser Arg Glu Arg Ala Asp Glu Pro Gln Trp Ser Leu Tyr Pro Ser
    130                 135                 140

Asp Ser Gln Val Ser Glu Glu Val Lys Thr Arg His Ser Glu Lys Ser
145                 150                 155                 160
```

-continued

```
Gln Arg Glu Asp Glu Glu Glu Glu Gly Glu Asn Tyr Gln Lys Gly
            165                 170                 175
Glu Arg Gly Glu Asp Ser Ser Glu Lys His Leu Glu Glu Pro Gly
        180                 185                 190
Glu Thr Gln Asn Ala Phe Leu Asn Glu Arg Lys Gln Ala Ser Ala Ile
        195                 200                 205
Lys Lys Glu Glu Leu Val Ala Arg Ser Glu Thr His Ala Ala Gly His
    210                 215                 220
Ser Gln Glu Lys Thr His Ser Arg Glu Lys Ser Ser Gln Glu Ser Gly
225                 230                 235                 240
Glu Glu Thr Gly Ser Gln Glu Asn His Pro Gln Glu Ser Lys Gly Gln
            245                 250                 255
Pro Arg Ser Gln Glu Glu Ser Glu Gly Glu Glu Asp Ala Thr Ser
        260                 265                 270
Glu Val Asp Lys Arg Arg Thr Arg Pro Arg His His His Gly Arg Ser
    275                 280                 285
Arg Pro Asp Arg Ser Ser Gln Gly Gly Ser Leu Pro Ser Glu Glu Lys
    290                 295                 300
Gly His Pro Gln Glu Glu Ser Glu Glu Ser Asn Val Ser Met Ala Ser
305                 310                 315                 320
Leu Gly Glu Lys Arg Asp His His Ser Thr His Tyr Arg Ala Ser Glu
            325                 330                 335
Glu Glu Pro Glu Tyr Gly Glu Glu Ile Lys Gly Tyr Pro Gly Val Gln
        340                 345                 350
Ala Pro Glu Asp Leu Glu Trp Glu Arg Tyr Arg Gly Arg Gly Ser Glu
        355                 360                 365
Glu Tyr Arg Ala Pro Arg Pro Gln Ser Glu Glu Ser Trp Asp Glu Glu
    370                 375                 380
Asp Lys Arg Asn Tyr Pro Ser Leu Glu Leu Asp Lys Met Ala His Gly
385                 390                 395                 400
Tyr Gly Glu Glu Ser Glu Glu Glu Arg Gly Leu Glu Pro Gly Lys Gly
            405                 410                 415
Arg His His Arg Gly Arg Gly Gly Glu Pro Arg Ala Tyr Phe Met Ser
        420                 425                 430
Asp Thr Arg Glu Glu Lys Arg Phe Leu Gly Glu Gly His His Arg Val
        435                 440                 445
Gln Glu Asn Gln Met Asp Lys Ala Arg Arg His Pro Gln Gly Ala Trp
    450                 455                 460
Lys Glu Leu Asp Arg Asn Tyr Leu Asn Tyr Gly Glu Glu Gly Ala Pro
465                 470                 475                 480
Gly Lys Trp Gln Gln Gln Gly Asp Leu Gln Asp Thr Lys Glu Asn Arg
            485                 490                 495
Glu Glu Ala Arg Phe Gln Asp Lys Gln Tyr Ser Ser His His Thr Ala
        500                 505                 510
Glu Lys Arg Lys Arg Leu Gly Glu Leu Phe Asn Pro Tyr Tyr Asp Pro
        515                 520                 525
Leu Gln Trp Lys Ser Ser His Phe Glu Arg Arg Asp Asn Met Asn Asp
    530                 535                 540
Asn Phe Leu Glu Gly Glu Glu Asn Glu Leu Thr Leu Asn Glu Lys
545                 550                 555                 560
Asn Phe Phe Pro Glu Tyr Asn Tyr Asp Trp Trp Glu Lys Lys Pro Phe
            565                 570                 575
```

```
Ser Glu Asp Val Asn Trp Gly Tyr Glu Lys Arg Asn Leu Ala Arg Val
            580                 585                 590

Pro Lys Leu Asp Leu Lys Arg Gln Tyr Asp Arg Val Ala Gln Leu Asp
        595                 600                 605

Gln Leu Leu His Tyr Arg Lys Lys Ser Ala Glu Phe Pro Asp Phe Tyr
        610                 615                 620

Asp Ser Glu Glu Pro Val Ser Thr His Gln Ala Glu Asn Glu Lys
625                 630                 635                 640

Asp Arg Ala Asp Gln Thr Val Leu Thr Glu Asp Glu Lys Lys Glu Leu
                645                 650                 655

Glu Asn Leu Ala Ala Met Asp Leu Glu Leu Gln Lys Ile Ala Glu Lys
            660                 665                 670

Phe Ser Gln Arg Gly
        675

<210> SEQ ID NO 2
<211> LENGTH: 11
<212> TYPE: PRT
<213> ORGANISM: Homo sapiens

<400> SEQUENCE: 2

Ala Asp Gln Thr Val Leu Thr Glu Asp Glu Lys
1               5                   10

<210> SEQ ID NO 3
<211> LENGTH: 115
<212> TYPE: PRT
<213> ORGANISM: Homo sapiens

<400> SEQUENCE: 3

Met Asn Ala Phe Leu Leu Ser Ala Leu Cys Leu Leu Gly Ala Trp Ala
1               5                   10                  15

Ala Leu Ala Gly Gly Val Thr Val Gln Asp Gly Asn Phe Ser Phe Ser
            20                  25                  30

Leu Glu Ser Val Lys Lys Leu Lys Asp Leu Gln Glu Pro Gln Glu Pro
        35                  40                  45

Arg Val Gly Lys Leu Arg Asn Phe Ala Pro Ile Pro Gly Glu Pro Val
    50                  55                  60

Val Pro Ile Leu Cys Ser Asn Pro Asn Phe Pro Glu Glu Leu Lys Pro
65                  70                  75                  80

Leu Cys Lys Glu Pro Asn Ala Gln Glu Ile Leu Gln Arg Leu Glu Glu
                85                  90                  95

Ile Ala Glu Asp Pro Gly Thr Cys Glu Ile Cys Ala Tyr Ala Ala Cys
            100                 105                 110

Thr Gly Cys
        115

<210> SEQ ID NO 4
<211> LENGTH: 16
<212> TYPE: PRT
<213> ORGANISM: Homo sapiens

<400> SEQUENCE: 4

Val Thr Val Gln Asp Gly Asn Phe Ser Phe Ser Leu Glu Ser Val Lys
1               5                   10                  15
```

```
<210> SEQ ID NO 5
<211> LENGTH: 211
<212> TYPE: PRT
<213> ORGANISM: Homo sapiens

<400> SEQUENCE: 5

Met Ile Ser Arg Met Glu Lys Met Thr Met Met Lys Ile Leu Ile
1               5                   10                  15

Met Phe Ala Leu Gly Met Asn Tyr Trp Ser Cys Ser Gly Phe Pro Val
            20                  25                  30

Tyr Asp Tyr Asp Pro Ser Ser Leu Arg Asp Ala Leu Ser Ala Ser Val
        35                  40                  45

Val Lys Val Asn Ser Gln Ser Leu Ser Pro Tyr Leu Phe Arg Ala Phe
    50                  55                  60

Arg Ser Ser Leu Lys Arg Val Glu Val Leu Asp Glu Asn Asn Leu Val
65                  70                  75                  80

Met Asn Leu Glu Phe Ser Ile Arg Glu Thr Thr Cys Arg Lys Asp Ser
                85                  90                  95

Gly Glu Asp Pro Ala Thr Cys Ala Phe Gln Arg Asp Tyr Tyr Val Ser
            100                 105                 110

Thr Ala Val Cys Arg Ser Thr Val Lys Val Ser Ala Gln Gln Val Gln
        115                 120                 125

Gly Val His Ala Arg Cys Ser Trp Ser Ser Thr Ser Glu Ser Tyr
    130                 135                 140

Ser Ser Glu Glu Met Ile Phe Gly Asp Met Leu Gly Ser His Lys Trp
145                 150                 155                 160

Arg Asn Asn Tyr Leu Phe Gly Leu Ile Ser Asp Glu Ser Ile Ser Glu
                165                 170                 175

Gln Phe Tyr Asp Arg Ser Leu Gly Ile Met Arg Val Leu Pro Pro
            180                 185                 190

Gly Asn Arg Arg Tyr Pro Asn His Arg His Arg Ala Arg Ile Asn Thr
    195                 200                 205

Asp Phe Glu
    210

<210> SEQ ID NO 6
<211> LENGTH: 12
<212> TYPE: PRT
<213> ORGANISM: Homo sapiens

<400> SEQUENCE: 6

Val Ser Ala Gln Gln Val Gln Gly Val His Ala Arg
1               5                   10

<210> SEQ ID NO 7
<211> LENGTH: 12
<212> TYPE: PRT
<213> ORGANISM: Homo sapiens

<400> SEQUENCE: 7

Val Asn Ser Gln Ser Leu Ser Pro Tyr Leu Phe Arg
1               5                   10

<210> SEQ ID NO 8
<211> LENGTH: 158
<212> TYPE: PRT
<213> ORGANISM: Homo sapiens
```

<400> SEQUENCE: 8

Met Met Gln Lys Leu Leu Lys Cys Ser Arg Leu Val Leu Ala Leu Ala
1               5                   10                  15

Leu Ile Leu Val Leu Glu Ser Ser Val Gln Gly Tyr Pro Thr Arg Arg
                20                  25                  30

Ala Arg Tyr Gln Trp Val Arg Cys Asn Pro Asp Ser Asn Ser Ala Asn
            35                  40                  45

Cys Leu Glu Glu Lys Gly Pro Met Phe Glu Leu Leu Pro Gly Glu Ser
    50                  55                  60

Asn Lys Ile Pro Arg Leu Arg Thr Asp Leu Phe Pro Lys Thr Arg Ile
65                  70                  75                  80

Gln Asp Leu Asn Arg Ile Phe Pro Leu Ser Glu Asp Tyr Ser Gly Ser
                85                  90                  95

Gly Phe Gly Ser Gly Ser Gly Ser Gly Ser Gly Ser Gly Ser Gly Phe
                100                 105                 110

Leu Thr Glu Met Glu Gln Asp Tyr Gln Leu Val Asp Glu Ser Asp Ala
                115                 120                 125

Phe His Asp Asn Leu Arg Ser Leu Asp Arg Asn Leu Pro Ser Asp Ser
            130                 135                 140

Gln Asp Leu Gly Gln His Gly Leu Glu Glu Asp Phe Met Leu
145                 150                 155

<210> SEQ ID NO 9
<211> LENGTH: 17
<212> TYPE: PRT
<213> ORGANISM: Homo sapiens

<400> SEQUENCE: 9

Asn Leu Pro Ser Asp Ser Gln Asp Leu Gly Gln His Gly Leu Glu Glu
1               5                   10                  15

Asp

<210> SEQ ID NO 10
<211> LENGTH: 352
<212> TYPE: PRT
<213> ORGANISM: Homo sapiens

<400> SEQUENCE: 10

Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
                20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
                100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
    130                 135                 140

```
Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
        195                 200                 205

Pro Gln Glu Glu Glu Gly Ser Gly Gly Gln Leu Val Thr Glu Val
        210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
                260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
        290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
                340                 345                 350

<210> SEQ ID NO 11
<211> LENGTH: 9
<212> TYPE: PRT
<213> ORGANISM: Homo sapiens

<400> SEQUENCE: 11

His His Gly Pro Thr Ile Thr Ala Lys
1               5

<210> SEQ ID NO 12
<211> LENGTH: 13
<212> TYPE: PRT
<213> ORGANISM: Homo sapiens

<400> SEQUENCE: 12

Gly Pro Met Phe Glu Leu Leu Pro Gly Glu Ser Asn Lys
1               5                   10
```

DIAGNOSTIC METHOD FOR INFLAMMATORY BOWEL DISEASE

This application is a U.S. National Phase Application of International Application No. PCT/AU2014/000682, filed Jun. 27, 2014, which claims priority to Australian Patent Application No. 2013902409, filed Jun. 28, 2013.

REFERENCE TO SEQUENCE LISTING

The Sequence Listing submitted Dec. 22, 2015 as a text file named "07082_0061U1_Sequence_Listing," created on Dec. 21, 2015, and having a size of 14,799 bytes is hereby incorporated by reference pursuant to 37 C.F.R. §1.52(e)(5).

FIELD OF THE INVENTION

The invention relates to a method for diagnosing or assessing an inflammatory bowel disease in a subject.

BACKGROUND

Inflammatory bowel diseases (IBD) are chronic immuno-inflammatory pathologies of the gastrointestinal tract. Crohn's Disease (CD) and Ulcerative colitis (UC) are known as inflammatory bowel diseases. These diseases are thought to be affected by many genetic and environmental factors, and have unknown aetiology. Clinical presentation is non-specific and diagnosis is based on a clinical, endoscopic, radiological and histological criteria. Disease course is characterised by relapses and remission. Symptoms are non-specific and include abdominal pain and diarrhea.

The clinical presentation of Crohn's Disease and Ulcerative colitis are similar. An accurate diagnosis of IBD, and the ability to discriminate between Crohn's Disease and Ulcerative colitis, is important in order to achieve effective treatment and management of the disease. There is currently no single diagnostic test for IBD. Invasive diagnostic investigations, in particular colonoscopy and histopathological evaluation of the inflamed gut wall, remain the standard tool for diagnosis. Colonoscopy is expensive and invasive, with a risk of bowel perforation. In particular, colonoscopy is not suitable for use in acute severe inflammation as the risk of bowel perforation is too high. Despite investigations using available methods, 15% of patients remain undifferentiated and are therefore termed as having indeterminate colitis.

Diagnostic antibody markers that have been tried include anti-*Saccharomyces cerevisae* antibody (ASCA) and perinuclear anti-neutrophil cytoplasmic antibody (P-ANCA). However, diagnosis with these markers is less effective due to their limited sensitivity and specificity.

What is needed is a convenient and reliable method for diagnosing and assessing IBD in subjects.

SUMMARY

A first aspect provides a method of diagnosing or assessing an inflammatory bowel disease (IBD) in a subject, comprising comparing the level of one or more markers in a tissue or body fluid of the subject relative to a reference value for the one or more markers, wherein the marker is selected from the group consisting of:
  i) Secretogranin-1 or a fragment thereof;
  ii) Guanylin or a fragment thereof;
  iii) SPP 24 or a fragment thereof;
  iv) AMBP or a fragment thereof; and
  v) Serglycin or a fragment thereof.

A second aspect provides a method of diagnosing or assessing an inflammatory bowel disease in a subject, comprising comparing the level of SPP 24 or a fragment thereof in a tissue or body fluid of the subject relative to a reference value for the one or more markers, wherein the reference value is the level of SPP 24 or a fragment thereof in a subject not suffering from IBD, and wherein IBD is diagnosed when the level of SPP 24 or a fragment thereof is elevated relative to the reference value.

A third aspect provides a method of diagnosing or assessing an inflammatory bowel disease in a subject, comprising comparing the level of serglycin or a fragment thereof in a tissue or body fluid of the subject relative to a reference value for serglycin, and wherein the reference value is the level of serglycin in a subject not suffering from IBD, and wherein IBD is diagnosed when the level of serglycin is reduced relative to the reference value.

A fourth aspect provides a method of diagnosing or assessing an inflammatory bowel disease in a subject, comprising comparing the level of one or more markers in a tissue or body fluid of the subject relative to a reference value for the one or more markers, wherein the one or more markers is selected from the group consisting of SPP 24 or a fragment thereof, and serglycin or a fragment thereof, and wherein the reference value is the level of the one or more markers in a subject not suffering from IBD, and wherein IBD is diagnosed when the level of SPP 24 or a fragment thereof is elevated relative to the reference value, and/or the level of serglycin or a fragment thereof is reduced relative to the reference value.

A fifth aspect provides a method of assessing whether a subject suffering from IBD is suffering from Crohn's Disease, comprising comparing the level of one or more markers selected from the group consisting of: secretogranin-1 or a fragment thereof; AMBP or a fragment thereof; and guanylin or a fragment thereof, in a tissue or body fluid of the subject relative to a reference value for the one or more markers, wherein the reference value is the level of the one or more markers in a subject suffering from Ulcerative colitis, and wherein Crohn's Disease is diagnosed when the level of the one or more markers is reduced relative to the reference value.

A sixth aspect provides a method of assessing whether a subject suffering from IBD is suffering from Ulcerative colitis, comprising comparing the level of one or more markers selected from the group consisting of secretogranin-1 or a fragment thereof and guanylin or a fragment thereof, in a tissue or body fluid of the subject relative to a reference value for the one or more markers, wherein the reference value is the level of the one or more markers in a subject suffering from Crohn's disease, and wherein Ulcerative colitis is diagnosed when the level of the one or more markers is increased relative to the reference value.

A seventh aspect provides a method of assessing whether a subject suffering from IBD is suffering from Ulcerative colitis, comprising comparing the level of guanylin or a fragment thereof in a tissue or body fluid of the subject relative to a reference value, wherein the reference value is the level of guanylin or a fragment thereof in a subject suffering from Crohn's disease, and wherein the patient is assessed as suffering from Ulcerative colitis when the level of guanylin or a fragment thereof is elevated relative to the reference value.

An eighth aspect provides a method of assessing the severity of Crohn's disease in a subject, comprising comparing the level of one or more markers selected from the group consisting of SPP 24 or a fragment thereof and secretogranin-1 or a fragment thereof in tissue or body fluid of the subject relative to a reference value for the one or more markers, wherein the reference value is the level of the one or more markers in a subject suffering from Crohn's disease of predetermined severity, and wherein the Crohn's disease is diagnosed as more severe than the Crohn's disease of predetermined severity when the level of the one or more markers is elevated relative to the reference value.

A ninth aspect provides a method of assessing the severity of Ulcerative colitis in a subject, comprising comparing the level of one or more markers selected from the group consisting of SPP24 or a fragment thereof and secretogranin-1 or a fragment thereof in tissue or body fluid of the subject relative to a reference value for the one or more markers, wherein the reference value is the level of the one or more markers in a subject suffering from Ulcerative colitis in remission, and wherein Ulcerative colitis is diagnosed as active when the level of secretogranin-1 or fragment thereof is elevated relative to the reference value, and/or the level of SPP24 or a fragment thereof is reduced relative to the reference value.

A tenth aspect provides a method of assessing the severity of IBD in a subject suffering from IBD, comprising comparing the level of secretogranin-1 or a fragment thereof in a tissue or body fluid of the subject relative to a reference value for secretogranin-1 or a fragment thereof, wherein the reference value is the level of secretogranin-1 or a fragment thereof in a subject suffering from IBD of predetermined severity, and wherein IBD is diagnosed as more severe than the IBD of predetermined severity when the level of secretogranin-1 or a fragment thereof is elevated relative to the reference value. In one embodiment, the IBD of predetermined severity is IBD in remission.

An eleventh aspect provides a method of assessing whether a subject with no symptoms or few symptoms of IBD is suffering from Ulcerative colitis in remission, comprising comparing the level of one or more markers selected from the group consisting of SPP24 or a fragment thereof and secretogranin-1 or a fragment thereof in a tissue or body fluid of the subject relative to a reference value, wherein the reference value is the level of the one or more markers in a subject suffering from active Ulcerative colitis, and wherein Ulcerative colitis in remission is diagnosed when the level of secretogranin-1 or fragment thereof is reduced relative to the reference value, and/or the level of SPP 24 or fragment thereof is elevated relative to the reference value.

A twelfth aspect provides a method for assessing whether a subject showing no symptoms or few symptoms of IBD is suffering from Crohn's disease or Ulcerative colitis in remission, comprising comparing the level of SPP 24 or a fragment thereof in a tissue or body fluid of the subject relative to a reference value, wherein the reference value is the level of the one or more markers in a subject not suffering from IBD, and wherein the subject is assessed as suffering from Crohn's disease in remission or Ulcerative colitis in remission when the level of SPP 24 or a fragment thereof is elevated relative to the reference value.

A thirteenth aspect provides a method of assessing whether a subject is suffering from active Ulcerative colitis or Ulcerative colitis in remission, comprising comparing the level of one or more markers selected from the group consisting of SPP 24 or a fragment thereof and secretogranin-1 or a fragment thereof, in a tissue or body fluid of the subject relative to a reference value for the one or more markers, wherein the reference value is the level of the one or more markers in a subject suffering from active Ulcerative colitis, and wherein the subject is assessed as suffering from ulcerative colitis in remission when the level of secretogranin-1 or fragment thereof is reduced relative to the reference value, and/or the level of SPP 24 or a fragment thereof is elevated relative to the reference value.

In one embodiment, a sample of the tissue or body fluid is obtained from the subject and the level of the one or more markers in the sample compared with the reference value.

An alternative aspect provides use of one or more markers selected from the group consisting of:
  i) Secretogranin-1 or a fragment thereof;
  ii) Guanylin or a fragment thereof;
  iii) SPP 24 or a fragment thereof;
  iv) AMBP or a fragment thereof; and
  v) Serglycin or a fragment thereof,
for diagnosing or assessing an IBD in a subject.

An alternative provides one or more markers selected from the group consisting of:
  i) Secretogranin-1 or a fragment thereof;
  ii) Guanylin or a fragment thereof;
  iii) SPP 24 or a fragment thereof;
  iv) AMBP or a fragment thereof; and
  v) Serglycin or a fragment thereof,
for use in diagnosing or assessing an IBD in a subject.

A fourteenth aspect provides a diagnostic device or protein array for diagnosing or assessing an IBD in a subject, comprising one or more markers selected from the group consisting of:
  (i) Secretogranin-1 or a fragment thereof;
  (ii) Guanylin or a fragment thereof;
  (iii) SPP 24 or a fragment thereof;
  (iv) AMBP or a fragment thereof; and
  (v) Serglycin or a fragment thereof,
  or an antibody or fragment thereof which specifically binds the one or more markers.

A fifteenth aspect provides one or more markers selected from the group consisting of:
  (i) Secretogranin-1 or a fragment thereof;
  (ii) Guanylin or a fragment thereof;
  (iii) SPP 24 or a fragment thereof;
  (iv) AMBP or a fragment thereof; and
  (v) Serglycin or a fragment thereof,
  for diagnosing or assessing an IBD in a subject.

A sixteenth aspect provides a kit for diagnosing or assessing an IBD in a subject, comprising one or more markers selected from the group consisting of:
  (i) Secretogranin-1 or a fragment thereof;
  (ii) Guanylin or a fragment thereof;
  (iii) SPP 24 or a fragment thereof;
  (iv) AMBP or a fragment thereof; and
  (v) Serglycin or a fragment thereof,
or an antibody or fragment thereof which specifically binds the one or more markers.

A seventeenth aspect provides a composition comprising one or more peptides selected from the group consisting of:

(i)
ADQTVLTEDEK
(SEQ ID NO: 2)

(ii)
VTVQDGNFSFSLESVK
(SEQ ID NO: 4)

(iii)
VSAQQVQGVHAR
(SEQ ID NO: 6)

-continued (iv)
                                                (SEQ ID NO: 7)
VNSQSLSPYLFR (v)
                                                (SEQ ID NO: 9)
NLPSDSQDLGQHGLEED (vi)
                                               (SEQ ID NO: 11)
HHGPTITAK.

An eighteenth aspect provides a method of diagnosing Ulcerative colitis in a subject, comprising comparing the level of one or more markers in a tissue or body fluid of the subject relative to a reference value for the one or more markers, wherein the one or more markers is selected from the group consisting of:
(i) secretogranin-1 or a fragment thereof;
(ii) guanylin or a fragment thereof;
wherein the reference value is the level of the one or more markers in a subject not suffering from IBD, and wherein Ulcerative colitis is diagnosed when the level of the one or more markers is elevated relative to the reference value.

An nineteenth aspect provides a method of diagnosing Crohn's disease in a subject, comprising comparing the level of a first marker and one or more second markers in a tissue or body fluid of the subject relative to a reference value for each of the markers, wherein the first marker is SPP24 or a fragment thereof and the second marker is selected from the group consisting of:
(ii) secretogranin-1 or a fragment thereof; and
(ii) guanylin or a fragment thereof;
wherein the reference value is the level of the first and second markers in a subject not suffering from IBD, and wherein Crohn's disease is diagnosed when the level of first marker is elevated relative to the reference value, and the level of the one or more second markers is not elevated relative to the reference value.

BRIEF DESCRIPTION OF THE DRAWINGS

FIG. 1 shows the full length amino acid sequence of A. human secretogranin-1 (SEQ ID NO: 1); B. human guanylin (SEQ ID NO: 3); C. human SPP 24 (SEQ ID NO: 5); D. human serglycin (SEQ ID NO: 8); and E. human AMBP (SEQ ID NO: 10). Peptides within the full length sequences that have been detected following MRM of enzyme digested samples and and/or ion count MS as described herein are underlined and in bold.

FIGS. 2A and 2B are graphs showing relative abundance of the peptide VSAQQVQGVHAR (SEQ ID NO: 6) and VNSQSLSPYLFR (SEQ ID NO: 7) in subjects suffering from IBD (IBD), subjects not suffering from IBD (C), and subjects suffering from rheumatoid arthritis (RA), as determined by MRM analysis of enzyme digested serum samples.

DETAILED DESCRIPTION

Figure 2C:
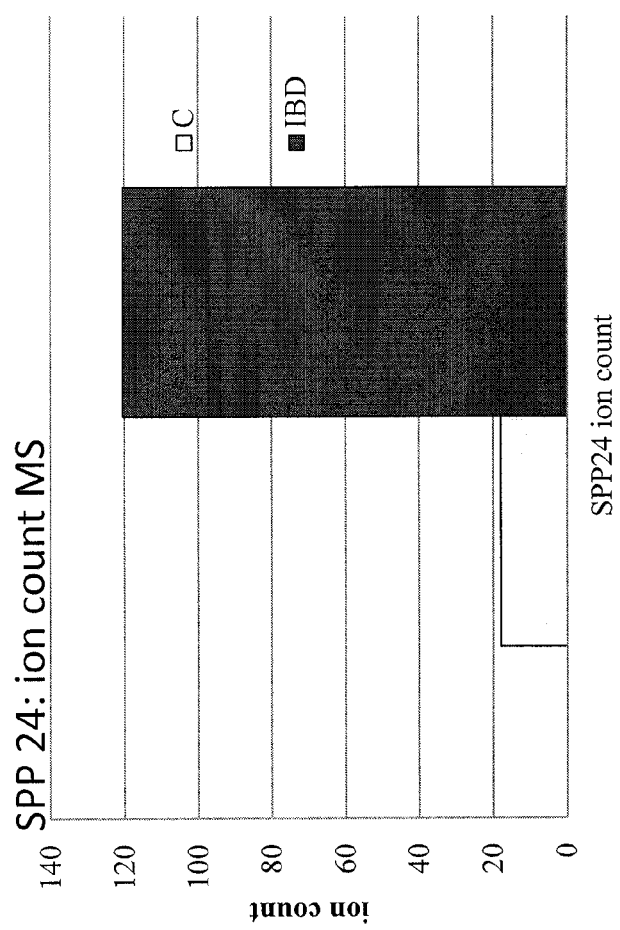
FIG. 2C is a graph of the relative abundance of the protein containing the peptide VSAQQVQGVHAR (SEQ ID NO: 6) and VSNQSLSPYLFR (SEQ ID NO: 7) in pooled serum samples from subjects suffering from IBD (IBD), or not suffering from IBD (control, C), as determined by ion count MS.

The invention relates in one aspect to a method of diagnosing or assessing an inflammatory bowel disease in a subject. The inflammatory bowel disease is diagnosed or assessed by comparing the level of one or more markers in tissue or body fluid of the subject relative to a reference value for the one or more markers.

As used herein, "Inflammatory bowel disease" refers to Crohn's disease and Ulcerative colitis, collectively. Crohn's disease (CD) is an inflammation anywhere along the digestive tract, including the large intestine, and involves all layers of the intestinal wall. Common symptoms of CD include chronic diarrhea fever, abdominal pain, weight loss and lack of appetite. Ulcerative colitis (UC) is an inflammation of the large intestine and is associated with ulcers in the inner layers of the lining of the large intestine. Common symptoms of UC include bloody diarrhea, fever and abdominal pain.

As used herein, a "marker" is a molecular indicator of a specific biological property or condition. A marker may be, for example, a protein, or a fragment of a protein such as a peptide.

The marker is selected from the group consisting of:
i) Secretogranin-1 or a fragment thereof;
ii) Guanylin or a fragment thereof;
iii) Spp24 or a fragment thereof;
iv) AMBP or a fragment thereof; and
v) Serglycin or a fragment thereof.

Secretogranin-1 is also known as Chromogranin-B. The full length amino acid sequence of human secretogranin-1 is shown in FIG. 1 (SEQ ID NO: 1). In embodiments in which the marker is secretogranin-1 or a fragment thereof, the secretogranin-1 or fragment thereof may:
i) comprise an amino acid sequence of SEQ ID NO: 1 or fragment thereof;
ii) comprise the amino acid sequence ADQTVLTEDEK (SEQ ID NO: 2);
iii) consist essentially of the amino acid sequence of SEQ ID NO: 2; or
iv) consist of the amino acid sequence of SEQ ID NO: 2.

Guanylin is also known as Guanylate cyclase activator 2A, and Guanylate cyclase activator 2. The full length amino acid sequence of human guanylin is shown in FIG. 1 (SEQ ID NO: 3). In embodiments in which the marker is Guanylin or a fragment thereof, the Guanylin or fragment thereof may:
i) comprise an amino acid sequence of SEQ ID NO: 3 or fragment thereof;
ii) comprise an amino acid sequence VTVQDGNFSFSLESVK (SEQ ID NO: 4);
iii) consist essentially of the amino acid sequence of SEQ ID NO: 4;
iv) consist of the amino acid sequence of SEQ ID NO: 4.

SPP24 is also known as secreted phosphoprotein 24 or secreted phosphoprotein 2. The full length amino acid sequence of human SPP24 is shown in FIG. 1 (SEQ ID NO: 5). In embodiments in which the marker is SPP24 or a fragment thereof, the SPP24 or fragment thereof may:
i) comprise an amino acid sequence of SEQ ID NO: 5 or fragment thereof;
ii) comprise an amino acid sequence VSAQQVQGVHAR (SEQ ID NO: 6);
iii) consist essentially of the amino acid sequence of SEQ ID NO: 6;
iv) consist of the amino acid sequence of SEQ ID NO: 6;
v) comprise an amino acid sequence VNSQSLSPYLFR (SEQ ID NO: 7);
vi) consist essentially of the amino acid sequence of SEQ ID NO: 7; or
vii) consist of the amino acid sequence of SEQ ID NO: 7.

Serglycin is also known as proteoglycan 1 core protein, secretory granule core protein, Hematopoietic proteoglycan core protein, Platelet proteoglycan core protein or secretory granule proteoglycan core protein. The full length amino acid sequence of human serglycin (SEQ ID NO: 8) is shown in FIG. 1. In embodiments in which the marker is Serglycin or a fragment thereof, the Serglycin or fragment thereof may:
i) comprise an amino acid sequence of SEQ ID NO: 8 or fragment thereof;
ii) comprise an amino acid sequence NLPSDSQDLGQHGLEED (SEQ ID NO: 9);
iii) comprise an amino acid sequence GPMFELLPGESNK (SEQ ID NO: 12);
iv) consist essentially of the amino acid sequence of SEQ ID NO: 9;
v) consist of the amino acid sequence of SEQ ID NO: 9;
vi) consist essentially of an amino acid sequence GPMFELLPGESNK (SEQ ID NO: 12);
vii) consist of the amino acid sequence of SEQ ID NO: 12.

AMBP or its cleavage products are also known as Alpha-1 microglycoprotein, alpha-1 microglobulin, inter-alpha-trypsin light chain, bikunin, EDC-1, HI-30, uronic acid-rich protein, trystatin. The full length amino acid sequence of AMBP is shown in FIG. 1 (SEQ ID NO: 10). In embodiments in which the marker is AMBP or a fragment thereof, the AMBP or fragment thereof may:
(i) comprise an amino acid sequence of SEQ ID NO: 10 or fragment thereof;
(ii) comprise an amino acid sequence HHGPTITAK (SEQ ID NO: 11);
(iii) consist essentially of the amino acid sequence of SEQ ID NO: 11; or
(iv) consist of the amino acid sequence of SEQ ID NO: 11.

As used herein, a "subject" is a mammal. The mammal can be a human, non-human primate, sheep, mouse, rat, dog, cat, horse, or any other mammals which can suffer from IBD. Typically, the subject is a human.

In one form, the invention relates to a method of diagnosing IBD is a subject. As used herein, "diagnosing IBD in a subject" refers to determining whether a subject is suffering from IBD. A subject suffering from IBD may be a subject suffering from active IBD, or a subject suffering from IBD in remission. A subject suffering from active IBD is a subject which is showing the symptoms of IBD. A subject suffering from IBD in remission is a subject who has suffered from the symptoms of IBD but which is not at the time of testing showing symptoms of IBD. A subject suffering from IBD in remission is suffering from quiescent IBD, and is not cured of the disease. In one embodiment, a subject suffering from IBD is a subject suffering from active IBD. In one embodiment, a subject suffering from IBD is a subject suffering from IBD in remission.

A subject suffering from Crohn's disease may be a subject suffering active Crohn's disease, or from Crohn's disease in remission. A subject suffering from Crohn's disease in remission is a subject who has suffered from the symptoms of Crohn's disease but which is not at the time of testing showing symptoms of Crohn's disease. A subject suffering from Crohn's disease in remission is suffering from quiescent Crohn's disease, and is not cured of the disease. In one embodiment, a subject suffering from Crohn's disease is a subject suffering from active Crohn's disease. In one embodiment, a subject suffering from Crohn's disease is a subject suffering from Crohn's disease in remission.

A subject suffering from Ulcerative colitis may be a subject suffering active Ulcerative colitis, or from Ulcerative colitis in remission. A subject suffering from Ulcerative colitis in remission is a subject who has suffered from the symptoms of Ulcerative colitis but which is not at the time of testing showing symptoms of Ulcerative colitis. A subject suffering from Ulcerative colitis in remission is suffering from quiescent Ulcerative colitis, and is not cured of the disease. In one embodiment, a subject suffering from Ulcerative colitis is a subject suffering from active Ulcerative colitis. In one embodiment, a subject suffering from Ulcerative colitis is a subject suffering from Ulcerative colitis in remission.

The inventors have found that secretogranin-1, Guanylin, SPP24, AMBP and serglycin, or peptides from these proteins, are markers of IBD, CD and/or UC in a subject. The markers are diagnostic of IBD, CD and/or UC. As described herein, the inventors have found that the level of peptides VSAQQVQGVHAR (SEQ ID NO: 6) from SPP24 and VNSQSLSPYLFR (SEQ ID NO: 7) from SPP24, are elevated, and that levels of the peptide NLPSDSQDLGQH-GLEED (SEQ ID NO: 9) from Serglycin, is reduced, following mass spectrometry (MS) analysis of enzyme digested serum samples from subjects suffering from IBD compared to the levels of the same peptides in serum samples of subjects not suffering from IBD. Thus, the inventors have reasoned that by determining the level of one or more of serglycin or a fragment thereof and/or SPP24 or a fragment thereof relative to levels in, for example, healthy control subjects, it can be determined whether a subject is suffering from IBD. As used herein, a "subject not suffering from IBD" is a subject who does not, and has not, suffered from IBD. Typically, a subject not suffering from IBD is a healthy subject. As used herein, a "healthy subject" is a subject not suffering from IBD or any other detectable inflammation.

In another form, the invention relates to assessing an IBD in a subject. As used herein, "assessing an IBD in a subject" refers to determining the severity of an IBD, or the type of IBD, in a subject. The type of IBD refers to whether the IBD is Crohn's disease or Ulcerative colitis. In one embodiment, the IBD is assessed in a subject known to be suffering from IBD. The inventors have found that the level of a secretogranin-1, and/or guanylin or a fragment thereof, in tissue or body fluid of a subject can be used to distinguish between Crohn's Disease and Ulcerative colitis. As described herein, the inventors have found that subjects suffering from Ulcerative colitis have increased levels of the peptides ADQTV-LTEDEK (SEQ ID NO: 2) from secretogranin-1, and VTVQDGNFSFSLESVK (SEQ ID NO: 4) from guanylin, relative to the level of these peptides in subjects suffering from Crohn's disease following MS analysis of enzyme digested serum samples. Accordingly, the inventors reason that increased levels of secretogranin-1 or a fragment thereof and/or guanylin or a fragment thereof, in a subject relative to the level of the peptide in a subject suffering from Crohn's disease is indicative of Ulcerative colitis.

As described herein, the inventors have also found that the levels of VTVQDGNFSFSLESVK (SEQ ID NO: 4) from guanylin are elevated in subjects suffering from Ulcerative colitis relative to the level of these peptides in subjects not suffering from IBD following MS analysis of enzyme digested serum samples. Accordingly, the inventors reason that increased levels of guanylin or a fragment thereof in a subject relative to the level of the peptide in a subject not suffering from IBD is indicative of Ulcerative colitis.

Moreover, as described herein, the inventors have found that increased levels of ADQTVLTEDEK (SEQ ID NO: 2) from secretogranin-1 are indicative of increased severity of Ulcerative colitis and Crohn's disease. The present invention therefore allows a determination of the prognosis of IBD in subjects suffering from IBD.

In one form, the invention relates to assessing whether a subject is not suffering from IBD (e.g. healthy), or whether a subject is suffering from IBD in remission. A subject suffering from IBD in remission is a subject who has previously suffered from symptomatic IBD but is not showing symptoms of IBD at the time of testing. As described herein, the inventors have found that MS analysis of enzyme digested serum samples from subjects suffering from Crohn's Disease or Ulcerative colitis in remission have elevated levels of VSAQQVQGVHAR (SEQ ID NO: 6) from SPP24 and VNSQSLSPYLFR (SEQ ID NO: 7) from SPP24 relative to healthy subjects, and subjects suffering from Ulcerative colitis in remission have elevated levels of VSAQQVQGVHAR (SEQ ID NO: 6) from SPP24, VNSQSLSPYLFR (SEQ ID NO: 7) from SPP24 and HHGPTITAK (SEQ ID NO: 11) from AMBP relative to healthy subjects. Accordingly, elevated levels of SPP24 or a fragment thereof in a subject showing no or few symptoms of IBD compared to levels of SPP24 or a fragment thereof in a healthy subject, are indicative that a subject is suffering from Ulcerative colitis or Crohn's disease in remission, and elevated levels of AMBP or a fragment thereof in a subject showing no or few symptoms of IBD relative to a healthy subject is indicative that the subject is suffering from Ulcerative colitis in remission.

In one embodiment, the one or more markers is selected from the group consisting of secretogranin-1 or a fragment thereof, Guanylin or a fragment thereof and SPP24 or a fragment thereof.

In one embodiment, the one or more markers is secretogranin-1 or a fragment thereof. In one embodiment, the one or more markers is Guanylin or a fragment thereof. In one embodiment, the one or more markers is a fragment of SPP24 comprising SEQ ID NO: 6. In one embodiment, the one or more markers is a fragment of SPP24 comprising SEQ ID NO: 7. In one embodiment, one or more markers is AMBP or a fragment thereof. In one embodiment, the one or more markers is serglycin or a fragment thereof.

In various embodiments, the one or more markers used to diagnose IBD is:
(a) Secretogranin-1 or a fragment thereof;
(b) Secretogranin-1 or a fragment thereof, Guanylin or a fragment thereof, and SPP24 or a fragment thereof;
(c) Secretogranin-1 or a fragment thereof, and Guanylin or a fragment thereof;
(d) Secretogranin-1 or a fragment thereof, and serglycin or a fragment thereof;
(e) Secretogranin-1 or a fragment thereof, and SPP24 or a fragment thereof;
(f) Guanylin or a fragment thereof;
(g) Guanylin or a fragment thereof, and SPP24 or a fragment thereof;
(h) Guanylin or a fragment thereof, and serglycin or a fragment thereof;
(i) Guanylin or a fragment thereof, and SPP24 or a fragment thereof, and serglycin or a fragment thereof;
(j) SPP24 or a fragment thereof, and serglycin or a fragment thereof;
(k) Secretogranin-1 or a fragment thereof, Guanylin or a fragment thereof, and serglycin or a fragment thereof;
(l) Secretogranin-1 or a fragment thereof, SPP24 or a fragment thereof, and serglycin or a fragment thereof;

(m) Secretogranin-1 or a fragment thereof, Guanylin or a fragment thereof, SPP24 or a fragment thereof, and serglycin or a fragment thereof;
(n) SPP24 or a fragment thereof;
(o) Secretogranin-1 or a fragment thereof, and SPP24 or a fragment thereof.

In one embodiment, the SPP24 or a fragment thereof is a fragment of SPP24 comprising SEQ ID NO: 6. In one embodiment, the SPP 24 or a fragment thereof is a fragment of SPP 24 comprising SEQ ID NO: 7.

In one embodiment, the Serglycin or a fragment thereof is a fragment of Serglycin comprising SEQ ID NO: 9. In another embodiment, the Serglycin or a fragment thereof is a fragment of serglycin comprising SEQ ID NO: 12.

In one embodiment, comparing the level of the one or more markers comprises determining the level of the one or more markers.

The level of the one or more markers of a subject may be determined by any known methods for determining the level of a protein in a tissue or body fluid. The method may be a direct method, in which the level of protein or fragment thereof is determined directly, or may be determined indirectly. Examples of direct methods include immunoassay and mass spectrometry. Examples of indirect methods include determining the level of expression of mRNA for a protein or peptide.

In one embodiment, the level of the one or more markers may be determined by obtaining a sample of the tissue or body fluid from the subject. The sample may be, for example, blood, serum, plasma, faeces, tissue, urine, tears, saliva, cells, organs, bone marrow, cerebrospinal fluid, sweat, bile, pancreatic juice, etc.

In one embodiment, the sample is a body fluid. The body fluid may be blood, serum, plasma, urine, feces, saliva, gastric juice, tears, sweat, bile, pancreatic juice. Typically, the body fluid is serum. As described herein, the inventors have found that the level of a peptide or protein comprising the amino acid sequence set forth in SEQ ID NOs: 1, 2, 3, 4, 5, 6, 7, 8, 9, 10, 11 and/or 12 in a serum sample from a subject can be used to diagnose whether a subject is suffering from IBD or to assess the severity or type of IBD. Thus, peptides or proteins comprising the amino acid sequence set forth in SEQ ID Nos: 1 to 12 are serum markers of IBD or the severity or type of IBD. The ability to use a serum sample provides a relatively convenient and rapid means by which to assess or diagnose IBD in a subject. As mentioned above, prior to the present invention, no markers were reliable for assessing or diagnosing IBD. The markers may be used individually, or a combination of the markers may be used, to diagnose or assess IBD.

In another embodiment, the sample is a tissue. The tissue may be any sample from the gastrointestinal tract, including rectum, colon, small intestinal tract. The sample may be all layers from the gastrointestinal tract, or may be the mucosal layer, or the epithelial layer.

Methods for obtaining tissue and body fluid samples from subjects are known in the art.

The sample may be processed to enhance detectability of the markers. For example, the sample may be fractionated to enrich for markers of a particular size range. In this regard, a sample may be fractionated to enrich for peptides or proteins of a particular size range. Methods for fractionation of peptides and proteins in a sample are known in the art and are described in, for example, Ly and 1JiJasinger (2008) Proteomics 8(20): pp 4197-4208; Echan et al. (2005) Proteomics 5: pp 3292-3303; Omenn (2005) Proteomics 5: pp 3226-3245. Examples of methods for size fractionation of peptides or proteins include size exclusion chromatography, ion exchange chromatography, affinity chromatography, gel electrophoresis. The sample may be processed to enrich for nucleic acid such RNA, more typically mRNA. Methods for enrichment of RNA, including mRNA, are known in the art and are described in Simpson R. J., ed. Proteins and Proteomics: a Lab Manual. 2003 Cold Spring Harbor Laboratory Press 926; Sambrook, J., Russet D.W., ed. Molecular Cloning: A Laboratory Manual Volume 1, 2, 3. 2001. Cold Spring Harbor Laboratory Press.

Once a sample has been obtained from the subject, the level of the one or more markers in the sample is compared with the reference value. The term "level" refers to an indication of abundance. Thus, the "level of one or more markers" refers to an indication of the abundance of one or more markers. The level of one or more markers may be a measure of the one or more markers, such as a measure of the amount of the one or more markers per unit weight or volume. The level of one or more markers may be a ratio, such as a ratio of the amount of one or more markers in a sample relative to the amount of the one or more markers of a reference value or in a control subject.

In one embodiment, the level of the one or more markers in a sample is the concentration of the one or more markers in the tissue or body fluid. The concentration of the one or more markers may be measured in any manner that is suitable for measuring concentrations of the marker in body fluids or tissue. For example, the level of the one or more markers may be determined using mass spectrometry or immunoassay.

In one embodiment, the level of the one or more markers in a sample may be determined using mass spectrometry. Examples of suitable mass spectrometry include: ionisation sources such as EI, CI, MALDI, ESI, and analysis such as Quad, ion trap, TOF, FT or combinations thereof, spectrometry, isotope ratio mass spectrometry (IRMS), thermal ionisation mass spectrometry (TIMS), spark source mass spectrometry, Multiple Reaction Monitoring (MRM) or SRM. The mass spectrometry may be conducted in combination with 2D gel electrophoresis, high performance liquid chromatography (HPLC) or other prefractionation or enrichment techniques. Methods for quantitation of molecules by two-dimensional gel electrophoresis, HPLC and mass spectrometry such as MALDI and SELDI are know in the art and are described in, for example, Simpson R. J., ed. Proteins and Proteomics: a Lab Manual. 2003 Cold Spring Harbor Laboratory Press; Sanchez, J. C. et al. Biomedical Applications of Proteomics 2004, Wiley-Blackwell. 425. Methods such as prefractionation are known and described in Ly and Wasinger (2008) Proteomics, 8(20): pp 4197-4208. Methods such as MRM are known in the art and described in, for example, Anderson and Hunter (2006) MCP, 5(4): pp. 573-589.

In one embodiment, the level of the one or more markers in a sample may be determined using MRM with a reverse-polynomial dilution (RPD) calibration or a stable-isotope dilution (SID) calibration. In one embodiment, the level of the one or more biomarkers in a sample is determined using RPD when MRM is used.

The level of the one or more markers may be determined using immunoassays. An immunoassay is an assay that uses an antibody to specifically bind to an antigen (e.g. the marker) The antibody may be a polyclonal, monoclonal, Fab, F(ab)$_2$, scFv, diabody, scFab etc. Immunoassays using antibodies include immunoblots, western blots, Enzyme linked Immunosorbant Assay (ELISA), Enzyme immunoassay (EIA), radioimmune assay. Immunoassay methods for detection and determination of levels of an antigen are known in the art and are described in, for example, Antibodies: A Laboratory Manual (1988); Monoclonal Antibodies: Principles and Practice (2nd Edition, 1986); Methods in Cell Biology: Antibodies in Cell Biology, volume 37 (Asai, ed. 1993) ; Basic Clinical Immunology (Stits & Terr, eds., $7^{th}$ ed. 1991). Generally, a sample obtained from a subject can be contacted with the antibody that specifically binds the marker. The antibody may be immobilised on a solid support such as a stick, plate, bead, microbead or array. A sample such as serum, blood, plasma, urine, or saliva is incubated with the antibodies for a period of time sufficient for the antibodies to bind the markers if present, and the mixture washed to remove unbound material. Sample bound to the antibody can then be determined by incubating the mixture with a detection agent such as, for example, a second antibody labelled with a detectable agent such as a fluorescent dye, radiolabels, enzymes (e.g. horseradish peroxidase, alkaline phosphatase, etc.), colloidal gold, etc. Alternatively, the marker in the sample can be detected using an indirect assay in which, for example, a second, labeled antibody is used to detect bound specific antibody, or in a competition or inhibition assay in which, for example, binding of the marker to a labelled specific antibody inhibits binding of the specific antibody to a detection site.

The level of the one or more markers in a sample may be determined indirectly by determining the expression of mRNA for the marker in a tissue sample. In this regard, there is typically a correlation between mRNA levels and protein expression. Accordingly, elevated or reduced levels of mRNA relative to a control is likely to reflect elevated or reduced levels of the protein encoded by that mRNA. The inventors therefore envisage that in some embodiments, the level of mRNA of one or more markers in tissue of a subject relative a reference value can be used to diagnose or assess IBD in a subject. Methods for assessing the levels of mRNA in a tissue sample include northern blot analysis, RT-PCR, real-time RT-PCR, array analysis. Such methods are known in the art and described in, for example, Sambrook, J., Russet D. W., ed. Molecular Cloning: A Laboratory Manual Volume 1, 2, 3. 2001. Cold Spring Harbor Laboratory Press; Rio, D. C. et al. RNA: A Lab Manual 2011, Cold Spring Harbor Laboratory Press.

The level of the one or more markers in the sample from the subject is compared with a reference value. The "reference value for the one or more markers" is a value which is indicative of the level of the one or more markers in a subject of predetermined disease status. The predetermined disease status may be, for example, not suffering from IBD (e.g. healthy), suffering from active IBD, suffering from IBD of predetermined severity (e.g. mild, moderate, severe, in remission), or suffering from IBD of a predetermined type, such as active Crohn's disease, Crohn's disease in remission, active Ulcerative colitis, Ulcerative colitis in remission.

The reference values may be a predetermined standard value. For example, the reference value may be a predetermined standard value, or a range of predetermined standard values, which represent no illness, or a predetermined type or severity of illness.

The reference value may be the level of the one or more markers in a reference sample from a subject, or a pool of subjects, not suffering from IBD or suffering from IBD or of a predetermined severity or type. As used herein, the "subject suffering from IBD of predetermined severity" is a subject suffering from IBD, the severity of which is known. For example, a subject may be suffering from IBD which is known to be mild, moderate, severe, or in remission. In some forms, the predetermined severity may be active. As used herein, "active" refers to disease which is not in remission, and may be mild, moderate or severe in severity. In some embodiments, the disease severity is as determined by a disease activity index (DAI) for CD or UC such as, for example, the Harvey-Bradshaw Index for CD, or the Ulcerative Colitis Disease Activity Index for UC. As used herein, a "subject suffering from IBD of a predetermined type" is a subject suffering from IBD in which the IBD is known to be either Crohn's Disease or Ulcerative colitis.

In one embodiment, the reference value is the level of the one or more markers in the tissue or body fluid of a subject, or subjects, having a predetermined disease status.

In one embodiment, the level of the one or more markers in a reference sample is the concentration of the one or more markers in the reference sample.

A reference sample may be from a subject not suffering from IBD. By comparing the level of the one or more markers in a tissue or body fluid of a subject with a level of the one or more markers from a reference sample obtained from a single subject, or a plurality of subjects, not suffering from IBD, it is possible to diagnose whether the subject is suffering from IBD, or the severity or type of IBD.

The reference sample may be from a subject suffering from IBD of a predetermined severity. In this regard, by comparing, for example, the level of SPP24 or a fragment thereof in a sample obtained from a subject suffering from IBD with a level of the one or more markers from a reference sample obtained from a subject suffering from a mild or less severe form of IBD, it is possible to determine the severity of the disease or whether the disease has progressed to a more severe form.

In various embodiments:
(a) The one or more markers is guanylin or a fragment thereof, wherein the reference value is the level of the one or more markers in the tissue or body fluid of a subject or subjects not suffering from IBD, and wherein Ulcerative colitis is diagnosed when the level of the one or more markers is elevated relative to the reference value.
(b) The one or more markers is SPP24 or a fragment thereof, wherein the reference value is the level of the one or more markers in the tissue or body fluid of a subject or subjects not suffering from IBD, and wherein IBD is diagnosed when the level of the one or more markers is elevated relative to the reference value.
(c) The one or more markers is serglycin or a fragment thereof, wherein the reference value is the level of the one or more markers in the tissue or body fluid of a subject or subjects not suffering from IBD, and wherein IBD is diagnosed when the level of the one or more markers is reduced relative to the reference value.
(d) The one or more markers is guanylin or a fragment thereof and SPP24 or a fragment thereof, wherein the reference value is the level of the one or more markers in the tissue or body fluid of a subject or subjects not suffering from IBD, and wherein Ulcerative colitis is diagnosed when the level of the one or more markers is elevated relative to the reference value.
(e) The one or more markers is SPP24 or a fragment thereof wherein the reference value is the level of the one or more markers in the tissue or body fluid of a subject or subjects not suffering from IBD, and wherein Ulcerative colitis is diagnosed when the level of the one or more markers is elevated relative to the reference value.
(f) The one or more markers is guanylin or a fragment thereof, and SPP24 or a fragment thereof, wherein the reference value is the level of the one or more markers in the tissue or body fluid of a subject or subjects not suffering from IBD, and wherein Crohn's disease is diagnosed when the level of SPP 24 or a fragment thereof is elevated relative to the reference value, and the level of Guanylin or a fragment thereof is not elevated relative to the reference value.

(g) The one or more markers is guanylin or a fragment thereof, and serglycin or a fragment thereof, wherein the reference value is the level of the one or more markers in the tissue or body fluid of a subject or subjects not suffering from IBD, and wherein Crohn's disease is diagnosed when the level of guanylin or a fragment thereof is not elevated relative to the reference value, and the level of serglycin or a fragment thereof is reduced relative to the reference value.

(h) The one or more markers is SPP24 or a fragment thereof, and serglycin or a fragment thereof, wherein the reference value is the level of the one or more markers in the tissue or body fluid of a subject or subjects not suffering from IBD, and wherein IBD is diagnosed when the level of SPP24 or a fragment thereof is elevated relative to the reference value, and the level of serglycin or a fragment thereof is reduced relative to the reference value.

(i) The one or more markers is guanylin or a fragment thereof, SPP 24 or a fragment thereof, and serglycin or a fragment thereof, wherein the reference value is the level of the one or more markers in the tissue or body fluid of a subject or subjects not suffering from IBD, and wherein Crohn's disease is diagnosed when the level of guanylin or a fragment thereof is not elevated relative to the reference value, the level of serglycin or a fragment thereof is reduced relative to the reference value, and the level of SPP24 or a fragment thereof is elevated relative to the reference value.

(j) The one or more markers is guanylin or a fragment thereof and SPP 24 or a fragment thereof, wherein the reference value is the level of the one or more markers in the tissue or body fluid of a subject or subjects not suffering from IBD, and wherein Crohn's disease is diagnosed when the level of guanylin or a fragment thereof is not elevated relative to the reference value, and the level of SPP24 or a fragment thereof is elevated relative to the reference value.

(k) The one or more markers is AMBP or a fragment thereof, wherein the reference value is the level of the one or more markers of a subject or subjects not suffering from IBD, and wherein Ulcerative colitis is diagnosed when the level of the one or more markers is elevated relative to the reference value.

(l) The one or more markers is SPP 24 or a fragment thereof, wherein the reference value is the level of the one or more markers in the tissue or body fluid of a subject or subjects suffering from Crohn's disease of predetermined severity, and wherein Crohn's disease is diagnosed as more severe than the Crohn's disease of predetermined severity when the level of the one or more markers is elevated relative to the reference value.

(m) The one or more markers is AMBP or a fragment thereof, wherein the reference value is the level of the one or more markers in the tissue or body fluid of a subject or subjects suffering from IBD of predetermined severity, and wherein IBD is diagnosed as more severe than the IBD of predetermined severity when the level of the one or more markers is elevated relative to the reference value.

(n) The one or more markers is secretogranin-1 or a fragment thereof, and the reference value is the level of secretogranin-1 or a fragment thereof in the tissue or body fluid of a subject or subjects suffering from ulcerative colitis, and wherein Crohn's Disease is diagnosed in a subject suffering from IBD when the level of secretogranin-1 or a fragment thereof is reduced relative to the reference value.

(o) The one or more markers is secretogranin-1 or a fragment thereof, and the reference value is the level of secretogranin-1 or a fragment thereof in the tissue or body fluid of a subject or subjects suffering from Crohn's Disease, and wherein ulcerative colitis is diagnosed when the level of secretogranin-1 or a fragment thereof is elevated relative to the reference value.

(p) The one or more markers is SPP 24 or a fragment thereof, and the reference value is the level of SPP 24 or a fragment thereof in the tissue or body fluid of a subject or subjects suffering from Ulcerative colitis of predetermined severity, and wherein Ulcerative colitis is diagnosed as more severe than the Ulcerative colitis of predetermined severity when the level of SPP 24 or fragment thereof is reduced relative to the reference value.

(q) The one or more markers is guanylin or a fragment thereof, and the reference value is the level of guanylin or a fragment thereof in the tissue or body fluid of a subject or subjects suffering from Crohn's disease, and wherein Ulcerative colitis is diagnosed when the level of guanylin is elevated relative to the reference value.

(r) The one or more markers is serglycin or a fragment thereof, and the reference value is the level of serglycin or a fragment thereof in the tissue or body fluid of a subject or subjects suffering from Crohn's disease of predetermined severity, and wherein Crohn's disease of the subject is diagnosed as more severe than the Crohn's disease of predetermined severity when the level of serglycin is reduced relative to the reference value.

(s) The one or more markers is secretogranin-1 or a fragment thereof, and the reference value is the level of the one or more markers in the tissue or body fluid of a subject or subjects suffering from Crohn's disease, and wherein Ulcerative colitis is diagnosed when the level of secretogranin-1 or a fragment thereof is elevated relative to the reference value.

(t) The one or more markers is AMBP or a fragment thereof, and the reference value is the level of the one or more markers in the tissue or body fluid of a subject or subjects suffering from Crohn's disease, and wherein Ulcerative colitis is diagnosed when the level of AMBP or a fragment thereof is elevated relative to the reference value.

(u) The one or more markers is SPP 24 or a fragment thereof, and the reference value is the level of the one or more markers in the tissue or body fluid of a subject or subjects suffering from Crohn's disease of predetermined severity, and wherein Crohn's disease is diagnosed as more severe when the level of SPP 24 of a fragment thereof is elevated relative to the reference value.

(v) The one or more markers is SPP 24 or a fragment thereof, and the reference value is the level of the one or more markers in the tissue or body fluid of a subject or subjects not suffering from IBD, and wherein Crohn's disease or Ulcerative colitis is diagnosed when the level of SPP 24 or a fragment thereof is elevated relative to the reference value.

(w) The one or more markers is Serglycin or a fragment thereof, and the reference value is the level of the one or more markers in the tissue or body fluid of a subject or subjects suffering from Crohn's disease in remission, and wherein Crohn's disease is diagnosed when the level of Serglycin or a fragment thereof is reduced relative to the reference value.
(x) The one or more markers is AMBP or a fragment thereof, and the reference value is the level of the one or more markers in the tissue or body fluid of a subject or subjects in remission from suffering from Crohn's disease or having mild Crohn's disease, and wherein severe Crohn's disease is diagnosed when the level of AMBP or a fragment thereof is elevated relative to the reference value.
(y) The one or more markers is guanylin or a fragment thereof, and the reference value is the level of the one or more markers in the tissue or body fluid of a subject or subjects suffering from Crohn's disease, and wherein Ulcerative colitis is diagnosed when the level of Guanylin or a fragment thereof is elevated relative to the reference value.
(z) The one or more markers is SPP 24 or a fragment thereof, and the reference value is the level of the one or more markers in the tissue or body fluid of a subject or subjects not suffering from IBD, and wherein Ulcerative colitis or Crohn's disease in remission is diagnosed when the subject is showing no or few symptoms of UC or CD and the level of SPP 24 or a fragment thereof is elevated relative to the reference value.
(aa) The one or more markers is Secretogranin-1 or a fragment thereof, AMBP or a fragment thereof, and SPP 24 or a fragment thereof, and the reference value is the level of the one or more markers in the tissue or body fluid of a subject or subjects suffering from Crohn's disease, and wherein Ulcerative colitis is diagnosed in a subject suffering from IBD when the level of the one or more markers is elevated relative to the reference value.
(bb) The one or more markers is AMBP or a fragment thereof, and SPP 24 or a fragment thereof, and the reference value is the level of the one or more markers in the tissue or body fluid of a subject or subjects suffering from Crohn's disease, and wherein Ulcerative colitis is diagnosed in a subject suffering from IBD when the level of the one or more markers is elevated relative to the reference value.
(cc) The one or more markers is Secretogranin-1 or a fragment thereof, and AMBP or a fragment thereof, and the reference value is the level of the one or more markers in the tissue or body fluid of a subject or subjects suffering from Crohn's disease, and wherein Ulcerative colitis is diagnosed in a subject suffering from IBD when the level of the one or more markers is elevated relative to the reference value.
(dd) The one or more markers is Secretogranin-1 or a fragment thereof, and SPP 24 or a fragment thereof, and the reference value is the level of the one or more markers in the tissue or body fluid of a subject or subjects suffering from Crohn's disease, and wherein Ulcerative colitis is diagnosed in a subject suffering from IBD when the level of secretogranin-1 or a fragment thereof is elevated relative to the reference value.
(ee) The one or more markers is Secretogranin-1 or a fragment thereof, AMBP or a fragment thereof, and SPP 24 or a fragment thereof, and the reference value is the level of the one or more markers in the tissue or body fluid of a subject or subjects suffering from Ulcerative colitis, and wherein Crohn's disease is diagnosed in a subject suffering from IBD when the level of secretogranin-1 or a fragment thereof and AMBP or a fragment thereof is reduced relative to the reference value.
(ff) The one or more markers is AMBP or a fragment thereof, and SPP 24 or a fragment thereof, and the reference value is the level of the one or more markers in the tissue or body fluid of a subject or subjects suffering from Ulcerative colitis, and wherein Crohn's disease is diagnosed in a subject suffering from IBD when the level of AMBP or a fragment thereof is reduced relative to the reference value.
(gg) The one or more markers is Secretogranin-1 or a fragment thereof, and AMBP or a fragment thereof, and the reference value is the level of the one or more markers in the tissue or body fluid of a subject or subjects suffering from Ulcerative colitis, and wherein Crohn's disease is diagnosed in a subject suffering from IBD when the level of the one or more markers is reduced relative to the reference value.
(hh) The one or more markers is Secretogranin-1 or a fragment thereof, and SPP 24 or a fragment thereof, and the reference value is the level of the one or more markers in the tissue or body fluid of a subject or subjects suffering from Ulcerative colitis, and wherein Crohn's disease is diagnosed in a subject suffering from IBD when the level of secretogranin-1 or a fragment thereof is reduced relative to the reference value.
(ii) The one or more markers is SPP 24 or a fragment thereof and AMBP or a fragment thereof and guanylin or a fragment thereof, and the reference value is the level of the one or more markers in the tissue or body fluid of a subject or subjects suffering from Crohn's disease, and wherein ulcerative colitis is diagnosed in a subject suffering from IBD when the level of the one or more markers is elevated relative to the reference value.
(jj) The one or more markers is a fragment of AMBP or a fragment thereof and guanylin or a fragment thereof, and the reference value is the level of the one or more markers in the tissue or body fluid of a subject or subjects suffering from Crohn's disease, or suffering from mild Crohn's disease, and wherein Crohn's disease is diagnosed in a subject suffering from IBD as severe when the level of the one or more markers is elevated relative to the reference value.
(kk) The one or more markers is serglycin or a fragment thereof, and the reference value is the level of the one or more markers in the tissue or body fluid of a subject or subjects suffering from Crohn's disease in remission, and wherein Crohn's disease is diagnosed in a subject suffering from IBD as active when the level of the one or more markers is reduced relative to the reference value.
(ll) The one or more markers is guanylin or a fragment thereof, and SPP24 or a fragment thereof, and the reference value is the level of the one or more markers in the tissue or body fluid of a subject or subjects not suffering from IBD, and wherein Ulcerative colitis is diagnosed when the level of the one or more markers is elevated relative to the reference value.
(mm) The one or more markers is SPP 24 or a fragment thereof, and the reference value is the level of SPP24 or a fragment thereof in the tissue or body fluid of a subject or subjects not suffering from IBD, and wherein Ulcerative colitis or Crohn's disease in remission is diagnosed in a subject showing no or few symptoms of IBD when the level of SPP 24 or a fragment thereof is elevated relative to the reference value. The one or more markers is AMBP or a fragment thereof, and the reference value is the level of AMBP in the tissue or body fluid of a subject or subjects not suffering from IBD, and wherein Ulcerative Colitis in remission is diagnosed in a subject showing no or few symptoms of IBD when the level of AMBP is elevated relative to the reference value.

(nn) The one or more markers is guanylin or a fragment thereof, and the reference value is the level of guanylin or a fragment thereof in the tissue or body fluid of a subject or subjects suffering from Crohn's disease, wherein Ulcerative colitis is diagnosed in a subject suffering from IBD when the level of guanylin or a fragment thereof is elevated relative to the reference value.

(oo) The one or more markers is guanylin or a fragment thereof, and the reference value is the level of guanylin or a fragment thereof in the tissue or body fluid of a subject or subjects not suffering from IBD, wherein Ulcerative colitis is diagnosed when the level of guanylin or a fragment thereof is elevated relative to the reference value.

(pp) The one or more markers is SPP24 or a fragment thereof and secretogranin-1 or a fragment thereof, and the reference value is the level of the one or more markers in the tissue or body fluid of a subject or subjects suffering from Crohn's Disease of a predetermined severity, wherein Crohn's Disease of greater severity than the predetermined severity is diagnosed in a subject suffering from Crohn's Disease when the level of the one or more markers is elevated relative to the reference value.

(qq) The one or more markers is SPP24 or a fragment thereof and/or secretogranin-1 or a fragment thereof, and the reference value is the level of one or more markers in the tissue or body fluid of a subject or subjects suffering from active Ulcerative Colitis, wherein Ulcerative Colitis in remission is diagnosed in a subject showing no or few symptoms of Ulcerative Colitis when the level of SPP24 or a fragment thereof is elevated relative to the reference value, and/or the level of secretogranin-1 or a fragment thereof is reduced relative to the reference value.

(rr) The one or more markers is SPP24 or a fragment thereof, and the reference value is the level of SPP24 or a fragment thereof in the tissue or body fluid of a subject or subjects not suffering from IBD, wherein IBD in remission is diagnosed in a subject showing no or few symptoms of IBD when the level of SPP24 or a fragment thereof is elevated relative to the reference value.

(ss) The one or more markers is secretogranin-1 or a fragment thereof, and the reference value is the level of secretogranin-1 or a fragment thereof in the tissue or body fluid of a subject or subjects suffering from IBD of predetermined severity, wherein IBD more severe than the predetermined severity is diagnosed in a subject when the level of secretogranin-1 or a fragment thereof is increased relative to the reference value.

(tt) The one or more markers is SPP 24 or a fragment thereof and Guanylin or a fragment thereof, a first reference value is the level of SPP24 or a fragment thereof in the tissue or body fluid of a subject not suffering from IBD, and a second reference value is the level of Guanylin of a fragment thereof in a subject or subjects suffering from CD, wherein UC in remission is diagnosed in a subject showing no or few symptoms of IBD when the level of SPP24 or a fragment thereof is elevated relative to the first reference value, and the level of guanylin or a fragment thereof is elevated relative to the second reference value.

In one form, Guanylin or a fragment thereof is the peptide VTVQDGNFSFSLESVK (SEQ ID NO: 4).

In one form, Secretogranin-1 or a fragment thereof is the peptide ADQTVLTEDK (SEQ ID NO: 2).

In one form, a fragment of SPP 24 comprising SEQ ID NO: 6 is the peptide VSAQQVQGVHAR (SEQ ID NO: 6).

In one form, Serglycine of a fragment thereof is the peptide NLPSDSQDLGQHGLEED (SEQ ID NO: 9) or the peptide GPMFELLPGESNK (SEQ ID NO: 12).

In one form, AMBP or a fragment thereof is the peptide HHGPTITAK (SEQ ID NO: 11).

In one form, a fragment of SPP 24 comprising SEQ ID NO: 7 is the peptide VNSQSLSPYLFR (SEQ ID NO: 7).

The methods described herein may be used independently of other diagnostic tests, or may be used in combination with other diagnostic tests.

As used herein, the term "elevated" means more than or greater than. Typically, a level "elevated relative to the reference value" is a level that is statistically significantly more than or greater than the reference level. A level may be elevated relative to a reference value by any amount that is statistically significant more than the reference value. Typically, levels greater than 1.2 fold are significant. In various embodiments, the level may elevated by about 1.2, 1.3, 1.4, 1.5, 1.6, 1.7, 1.8, 1.9, 2.0 fold or greater.

As used herein, the term "reduced" means less than or lower than. Typically, a level "reduced relative to the reference value" is a level that is statistically significantly less than or lower than the reference level. A level may be reduced relative to a reference value by any amount that is statistically significant less than the reference value. Typically, levels that are reduced by than 1.2 fold or more are significant. In various embodiments, the level may reduced by about 1.2, 1.3, 1.4, 1.5, 1.6, 1.7, 1.8, 1.9, 2.0 fold or greater.

As used herein, the term "not elevated" means not statistically significantly more than or greater than. A level that is "not elevated relative to the reference value" may be a level that is not statistically significantly more than the reference value, or is less than the reference value. Statistical significance may be determined by any methods known in the art, such as, for example, a student t test.

In one embodiment, the method of diagnosing or assessing comprises the further step of treating the subject for IBD, UC or CD if the subject is diagnosed or assessed as suffering from IBD, UC or CD. Methods for the treatment of IBD, CD and UC are known in the art and are described in, for example, D. C. Baumgart, Sandborn, W. J., Inflammatory bowel disease: clinical aspects and established and evolving therapies, The Lancet 369 (2007) 1641-1657. Treatments for UC and CD include administration of anti-inflammatory agents such as 5-aminosalicylic acid, mesalazine, sulfasalazine, mesalamine, olsalazine, balsalazide; corticosteroids; immune modifiers such as thiopurines such as 6-mercaptopurine, azathioprine, calineurin inhibitors such as cyclosporine A, tacrolimus; methotrexate, anti-TNF agents such as infliximab, adalimumab, certolizumab, as well as dietary management.

The invention further relates to a diagnostic peptide selected from the group consisting of: ADQTVLTEDK (SEQ ID NO: 2); VTVQDGNFSFSLESVK (SEQ ID NO: 4); VSAQQVQGVHAR (SEQ ID NO: 6); VNSQSLSPYLFR (SEQ ID NO: 7); NLPSDSQDLGQH-GLEED (SEQ ID NO: 9); HHGPTITAK (SEQ ID NO: 11). In one embodiment, the diagnostic peptides are isotopically labelled. The peptides may be labelled with any isotope suitable for use in mass spectrometry. The isotope may be, for example, $C^{13}$ or $C^{13}$ and $N^{15}$.

The invention further relates to a composition comprising one or more peptides selected from the group consisting of: secretogranin-1 or a fragment thereof, such as ADQTVLT- EDK (SEQ ID NO: 2); guanylin or a fragment thereof, such as VTVQDGNFSFSLESVK (SEQ ID NO: 4); SPP 24 or a fragment thereof, such as VSAQQVQGVHAR (SEQ ID NO: 6) or VNSQSLSPYLFR (SEQ ID NO: 7); Serglycin or a fragment thereof, such as NLPSDSQDLGQHGLEED (SEQ ID NO: 9); AMBP or a fragment thereof, such as HHGPTITAK (SEQ ID NO: 11). In one embodiment, the diagnostic peptides are isotopically labelled. The peptides may be labelled with any isotope suitable for use in mass spectrometry. The isotope may be, for example, $C^{13}$ or $C^{13}$ and $N^{15}$.

The invention further relates to kits for diagnosing or assessing IBD in a subject. The kits can be used to carry out the method of the invention. In one form, the kit comprise antibodies which specifically bind to the one or more markers. In another form, the kit comprises nucleic acid such as primers for amplifying the one or more markers using, for example, RT-PCR, or probes, for detection of mRNA. In another form, the kits comprise peptides from the one or more markers for use in mass spectrometry.

The kits may comprise a control sample such as a sample from a subject or subjects not suffering from IBD, or suffering from IBD of a predetermined severity or type. Kits comprising antibodies may comprise a solid support on which the antibody is immobilised, and a second antibody conjugated to a detectable group. Kits comprising nucleic acids may comprise fluorescent labels for detection of hybridisation. The kits may comprise solid supports such as arrays or beads.

Typically, the kits comprise instructions for use.

In the claims which follow and in the preceding description of the invention, except where the context requires otherwise due to express language or necessary implication, the word "comprise" or variations such as "comprises" or "comprising" is used in an inclusive sense, ie. to specify the presence of the stated features but not to preclude the presence or addition of further features in various embodiments of the invention. It must be noted that as used herein and in the appended claims, the singular forms "a", "an", and "the" include plural reference unless the context clearly dictates otherwise. Thus, for example, a reference to "a peptide" includes a plurality of such peptides, and so forth. Unless defined otherwise, all technical and scientific terms used herein have the same meanings as commonly understood by one of ordinary skill in the art to which this invention belongs.

The invention will now be further described by way of reference only to the following non-limiting examples. It should be understood, however, that the examples following are illustrative only, and should not be taken in any way as a restriction on the generality of the invention described above.

EXAMPLES

Example 1

Discovery Phase, Identification of Diagnostic Markers for Differentiation Between Healthy and IBD and UC and CD as Well as Severity Sample Pooling and Preparation Prior to MF10 Fractionation Five plasma samples, 30 µL each, were pooled into each group defined by their clinical activity with the addition of 15 µL of 10% protease inhibitor (Roche, Basel, Switzerland) resulting in 11 pools of grouped samples as listed below in Table-1. Prior to the MF10 fractionation, the pooled samples were diluted with 150 µL of 180 mM Tris/20 mM EACA/4M urea buffer, pH 10.2 and centrifuged for 10 minutes to isolate the supernatant from the plasma debris.

Table-1. Disease characteristics of pooled group samples. Each pool was an equal mix of 5 patients based on the concentration of total protein.

TABLE 1

| Healthy control group | Clinical Remission group | Mild clinical activity group | Moderate-severe clinical activity group |
|---|---|---|---|
| Control Pool A | UC pool A | UC pool B | UC pool D |
| Control Pool C | CD pool A | UC pool C | CD pool E |
| | CD pool C | CD pool B | |
| | | CD pool D | |

MF10 Partitioning Methods

MicroFlow MF10 (NuSep, Frenchs Forest, Sydney, Australia) presents a unique in-solution electrophoresis method to enrich for low mass proteins. Proteins less than 25 kDa are an area of the proteome that are not well explored and challenging to detect using 2D-SDS-PAGE or LCMS methods. MF10 allows for the enrichment of this often omitted section of the proteome. MicroFlow MF10 (NuSep, Frenchs Forest, Sydney, Australia) partitioning methods were done as per the methods described in Ly and Wasinger (2008) Proteomics, 8(20): pp. 4197-4208. Any modifications made to the description are mentioned in brief. For protein separation, we used a 5 chamber cartridge assembly method using 5, 25, 45, 65 and 125 kDa polyacrylamide membranes (NuSep, French Forest, Sydney, Australia) and 1 kDa regenerated cellulose membrane (Millipore, Massachusetts, USA), resulting in the following fractions; F1, F2, F3, F4 and F5. This essentially created 1 kDa to 25 kDa fractions of enriched plasma proteins. These cartridge assemblies have 2 separate lanes of chambers which allow two different samples to be fractionated simultaneously.

MF10 Pooled Plasma Fractionation

The cartridge assemblies were loaded to the separation unit of MF10 with 100 mL of 90 mM Tris/10 mM EACA/2M urea buffer, pH 10.2 circulating around the electrodes for 10 minutes prior to sample loading. One hundred and forty micro liters of the pooled plasma sample was loaded onto both lanes of the F1 chamber and for the 2×4 remaining chambers, 140 µL of 90 mM Tris/10 mM EACA/2M urea buffer, ph 10.2 was loaded. Fractionation was performed first at 50V for 30 mins followed by 250V for 2 h 30 mins at 15° C. After the separation, each fraction from both lanes was collected using gel-loading tips and pooled together to give 5 distinct mass defined fractions.

Trypsin Digestion and Sample Preparation for LC-MS/MS

Fraction 4 and 5 samples were cleaned with C18 stage tips (Proxeon, Odense, Denmark), speedvac dried and rehydrated with 50 µL of 50 mM ammonium bicarbonate, pH 8.0. Fraction 1, 2 and 3 samples were acetone precipitated, cold centrifuged and the dry pellets were rehydrated in 200 µL of 50 mM ammonium bicarbonate, pH 8.0 for fraction 1 and 2, and 100 µL for fraction 3. Subsequently, trypsin was added to all fractions at a ratio of approximately 1:100, trypsin/total protein and incubated overnight at 37° C. Following digestion, 4 µL of formic acid was added to stop the reaction and the samples were speedvac dried. All fractions were re-suspended in 10 µL of buffer A (2% acetic acid, 0.1% formic acid) prior to LC-MS/MS. One micro liter of F5, 0.5 μL of F4, 0.2 μL of F3 and 0.1 μL of F1 and F2 each were loaded onto the nano-LC.

LC-MS/MS Configuration

An LTQ-FT Ultra mass spectrometer (Thermo Electron, Bremen, Germany) was used to analyze the plasma fractions. As per Ly and Wasinger (2008), peptides were separated by nano-LC using an Ultimate 3000 HPLC and autosampler system (Dionex, Amsterdam, Netherlands).14 1800V was applied to low volume tee (Upchurch Scientific, WA, USA) and the column tip was positioned ~0.5 cm from the heated capillary (T=200° C.) of the LTQ-FT. The instrument operated in DDA mode, with positive ions generated by electrospray. A survey scan of m/z 350-1750 was acquired in the FT ICR cell. Collision induced dissociation was used by the linear ion trap in which up to seven of the most abundant ions (>2000 counts) with charge states of +2 or +3 were successively isolated and fragmented. Mass to charge ratios selected for MS/MS were dynamically excluded for 60 seconds. 'Mascot Daemon/extract_msn' (Matrix Science, London, England) was used with default parameters to generate peak lists, which were submitted to the database search program Mascot. MS was then repeated depending on the technical variations observed. Most fractions required under 3 repeats.

Protein Database Search, Identification and Assessment

The Swiss prot release 15 protein database was searched using the Mascot search algorithm with 6 ppm peptide tolerance, 0.6 Da fragment tolerance, and no enzyme selected. Progenesis LC-MS version 2.4 (Nonlinear Dynamics, Newcastle upon Tyne, UK) was used to simultaneously compare and assess for differential abundance based on peptide ion counting. A statistical model, analysis of variance (ANOVA), was used to calculate the p-values of differential abundances. Briefly, ion intensity maps from each run were aligned to a reference sample and ion feature matching was achieved by aligning consistent ion m/z and retention times. The peptide intensities were normalized against total intensity (sample specific log-scale abundance ratio scaling factor) and compared between groups by one-way analysis of variance (ANOVA, P≤0.05 for statistical significance) and post hoc multiple comparison procedures. Type I errors were controlled for by False Discovery Rate (FDR) with q value significance set at 0.01. Peptides exhibiting a statistically significant 1.5-fold or greater abundance difference between groups were identified using the database search program Mascot (Matrix Science, London, UK, www.matrixscience.com). MS/MS spectra of differentiating peptides were searched against the Swiss-Prot database (version 15) using Mascot. Parent and fragment ions were searched with tolerances of ±4 ppm and ±0.5 Da, respectively. Peptide charge states were set at +2 and +3. 'No enzyme' was specified. Proteins and peptides were considered confidently identified when matches had a high ion score>20 and were statistically significant and at least semi-tryptic. Following identification a filter was applied to select proteins of human origin.

These hypothesis-free proteomic analysis of differences between control, Crohns disease and Ulcerative colitis patients resulted in the analysis of over 11,000 ions for differential assessment; the majority of which as expected remained at the same abundance levels between the groups. 58 proteins were identified as significantly (p<0.05) different in abundance levels and 6 peptides were chosen from this hypothesis-free experiment for further validation using MRM. These peptides were ADQTVLTEDK (SEQ ID NO: 2) from Secretogranin-1, VTVQDGNFSFSLESVK (SEQ ID NO: 4) from Guanylin, VSAQQVQGVHAR (SEQ ID NO: 6) from SPP 24, VNSQSLSPYLFR (SEQ ID NO: 7) from SPP 24, NLPSDSQDLGQHGLEED (SEQ ID NO: 9) from Serglycin; and HHGPTITAK (SEQ ID NO: 11) from AMBP.

Example 2

Absolute Quantitation of Chosen Diagnostic Markers for Differentiation Between Healthy, IBD, CD and UC as Well as Severity 2.1 Plasma and Serum Samples A total of 104 participants, including 56 CD patients, 27 UC patients, 9 healthy controls and 12 rheumatoid arthritis (RA) patients, were recruited. All IBD and RA patients were recruited from IBD and RA outpatient clinics at Bankstown-Lidcombe and Concord Repatriation General Hospitals, New South Wales, Australia. All participants provided written informed consent before partaking in this study. All IBD patients had been previously diagnosed with CD or UC according to standard clinical, endoscopic and histological criteria. Disease activity at the time of recruitment was assessed using the Crohn's Disease Activity Index for patients with CD and the partial Mayo score for patients with UC. All RA patients had been previously diagnosed by a rheumatologist according to standard criteria. Subject details and disease characteristics were obtained at time of recruitment, and are shown in Table 2.

TABLE 2

| | Participant characteristics | | | |
|---|---|---|---|---|
| | Group (participants) | | | |
| | Crohn's Disease (n = 56) | Ulcerative Colitis (n = 27) | Healthy Controls (n = 9) | Rheumatoid arthritis (n = 12) |
| Plasma samples obtained | 59 | 32 | 9 | 12 |
| Mean Age (±SD) | 37 (±15) | 39 (±15) | 31 (±11) | 56 (±14) |
| Males (%) | 30 (51%) | 10 (31%) | 3 (25%) | 3 (33%) |
| Females (%) | 29 (49%) | 22 (69%) | 9 (75%) | 6 (67%) |
| Disease activity at collection | | | | |
| Remission | 27 (47%) | 11 (34%) | | |
| Mild activity | 18 (30%) | 9 (28%) | | |
| Moderate activity | 8 (13%) | 5 (16%) | | |
| Severe activity | 6 (10%) | 7 (22%) | | |
| Disease phenotype | | | | |
| Inflammatory | 19 (32%) | | | |
| Stricturing | 15 (25%) | | | |
| Penetrating | 25 (42%) [18[a]] | | | |

[a]This includes 18 samples collected from patients with penetrating phenotype and perianal disease.

Blood samples were collected by standard venepuncture technique with EDTA-vacutainers. Samples were centrifuged immediately for 10 minutes at 4000 revolutions per minute at room temperature to isolate the plasma from the cellular components of the blood. The plasma was immediately extracted and stored at −80° C. in 100 μL aliquots. A second plasma sample was collected from 8 patients when they developed changes in their disease profile at subsequent consultations.

Development of MRM Method

Candidate peptides were selected based on LC-MS/MS experiments described in Example 1. Skyline software v1.3

(MacCoss Lab, Washington, USA) and MS/MS spectra from previous LC-MS/MS experiments were used to generate a scheduled MRM method consisting of 4-7 transitions per peptide.

Stable Isotope-Labelled Peptides

Synthetic light and $^{13}$C-labelled heavy peptides for each candidate peptide were obtained in powder form from Sigma-Aldrich (Missouri, USA) at greater than 95% purity and dissolved in 0.1% TFA and 5% formic acid to a 1 mg/ml concentration.

Standard Curve Generation

Serial dilutions of each light synthetic peptide were prepared and made up to a final volume of 10 μL. Standard curves were prepared within the previously established linear working range of each peptide. Heavy peptides were spiked into each dilution (and patient sample) at the same concentration for normalisation of technical variability.

Sample Preparation for MRM

Individual patient samples were analysed by MRM. A plasma volume of 2 μL from each sample was added to 48 μL of ammonium bicarbonate 50 mM, pH8 and digested overnight at 37° C. with 1 μg Trypsin. Five μL of formic acid was added to end digestion and samples were dried down in a SpeedVac and resuspended in 0.1% formic acid. Peptide samples were purified using 2 passes through C18 Stage tips (ThermoScientific, Illinois, USA) and dried down. Cleaned peptide samples were then resuspended in 10 μL of 0.1% formic acid and heavy labelled peptides added to a final concentration of 100 fmol/μL.

MRM Analysis

Two μL injections of each sample was analysed in a 4000 Q-Trap mass spectrometer (AB SCIEX, Massachusetts, USA) coupled to an Ultimate 3000 HPLC and autosampler system (Dionex, Amsterdam, Netherlands) for the selected transitions.

MRM Data Analysis

MRM data were processed using Skyline software v1.3 (MacCoss Lab, Washington, USA). For each target peptide, relative quantitation was performed by ratio comparison of total transition peak areas between samples. Absolute quantitation was performed by normalization of peak areas to the heavy isotope internal standard, and concentration calculated according to the constructed standard curves for each peptide.

SPSS Statistics 20 program (IBM, New York, USA) was used for statistical analysis to perform Kruskal-Wallis tests, Mann-Whitney U tests and Spearman's rank correlation, and generate receiver operating characteristic (ROC) curves.

Experiment 3

Confirmation of Proteins/Peptides

LC-MS/MS Using LTQ-FT Instruments

An LTQ-FT Ultra mass spectrometer (Thermo Electron, Bremen, Germany) was used to analyse protein band fractions. As per Ly and Wasinger [9], peptides were separated by nano-LC using an Ultimate 3000 HPLC and autosampler system (Dionex, Amsterdam, Netherlands). 1800V was applied to low volume tee (Upchurch Scientific, WA, USA) and the column tip positioned ~0.5 cm from the heated capillary (T=200° C.) of a LTQ-FT. The instrument operated in DDA mode, with positive ions generated by electrospray. A survey scan of m/z 350-1750 was acquired in the FT ICR cell.

Collision induced dissociation was used by the linear ion trap in which up to seven of the most abundant ions (>2000 counts) with charge states of +2 or +3 were successively isolated and fragmented. Mass to charge ratios selected for MS/MS were dynamically excluded for 60 seconds.

Identification and Assessment of Proteins

'Mascot Daemon/extract_msn' (Matrix Science, London, England) was used with default parameters to generate peak lists, which were submitted to the database search program Mascot. The Swiss-Prot release 15 protein database was searched using the Mascot search algorithm with 6 ppm peptide tolerance, 0.6 Da fragment tolerance, and no enzyme selected.

4. Results a. Peptides which Diagnose IBD

Figure 3:
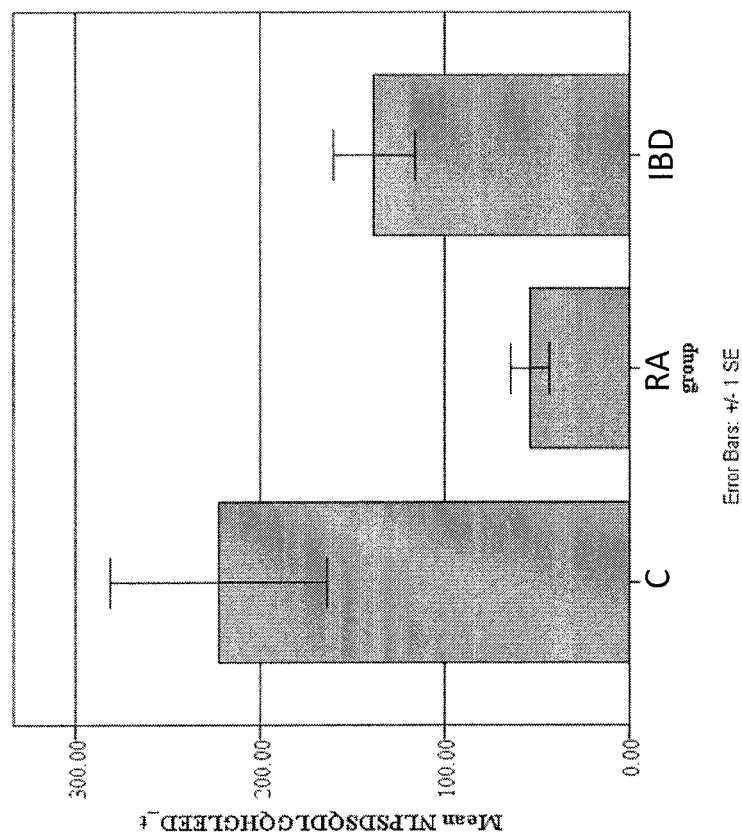
FIG. 3 is a graph showing the relative abundance of the peptide NLPSDSQDLGQHGLEED (SEQ ID NO: 9) in subjects suffering from TBD (IBD), subjects not suffering from IBD (C), and subjects suffering from rheumatoid arthritis (RA), as determined by MRM analysis of enzyme digested serum samples.

The absolute abundance of peptides in samples from healthy patients (C) or patients suffering from IBD (IBD) or rheumatoid arthritis (RA) as determined by MRM is shown in FIGS. 2A and 2B, or by relative abundance ion count is shown in FIGS. 2C and 3.

As can be seen from FIGS. 2A, 2B, and 2C, levels of the peptides VSAQQVQGVHAR (SEQ ID NO: 6) and VNSQSLSPYLFR (SEQ ID NO: 7) from SPP 24, are elevated in serum from patients suffering from IBD as compared to levels of the same peptides in control patients (i.e. patients not suffering from IBD).

Referring to FIG. 3, it can be seen that absolute abundance levels of the peptide NLPSDSQDLGQHGLEED (SEQ ID NO: 9) from Serglycin is reduced in serum from patients suffering from IBD as compared to levels of the same peptides in control patients (i.e. patients not suffering from IBD).

b. Peptides which Distinguish Between Ulcerative Colitis and Crohn's Disease

Figure 4A:
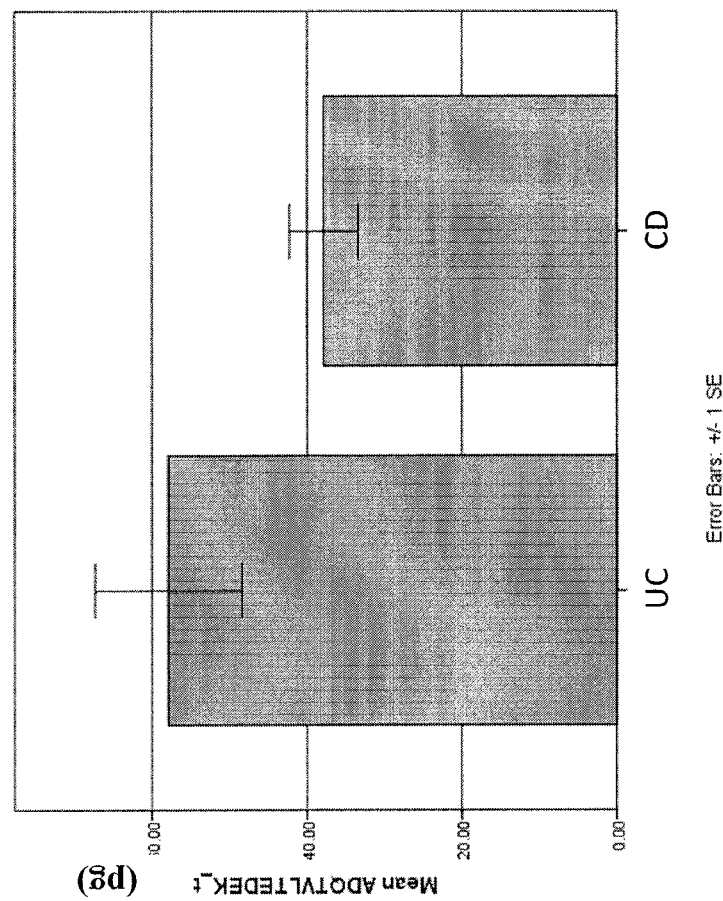
FIGS. 4A and 4B and 4C are graphs showing the relative abundance of: A. ADQTVLTEDEK (SEQ ID NO: 2); and B. HHGPTITAK (SEQ ID NO: 11); and C. VTVQDGNFSFSLESVK (SEQ ID NO: 4), in subjects suffering from Ulcerative colitis (UC) or Crohn's disease (CD), as determined by MRM analysis of trypsin digested serum samples.
Figure 4B:
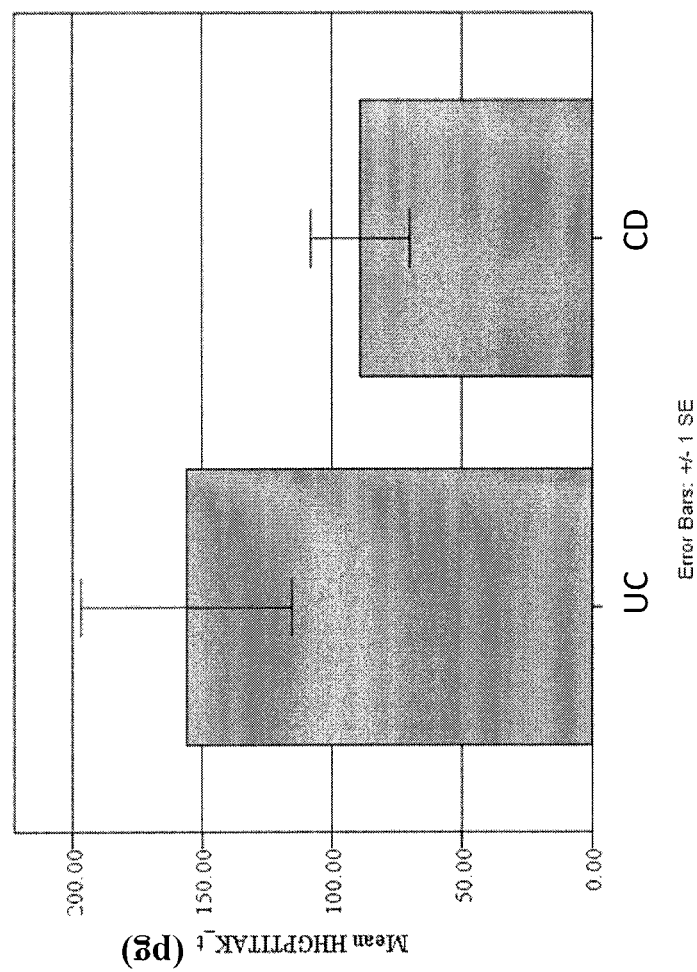
Figure 4C:
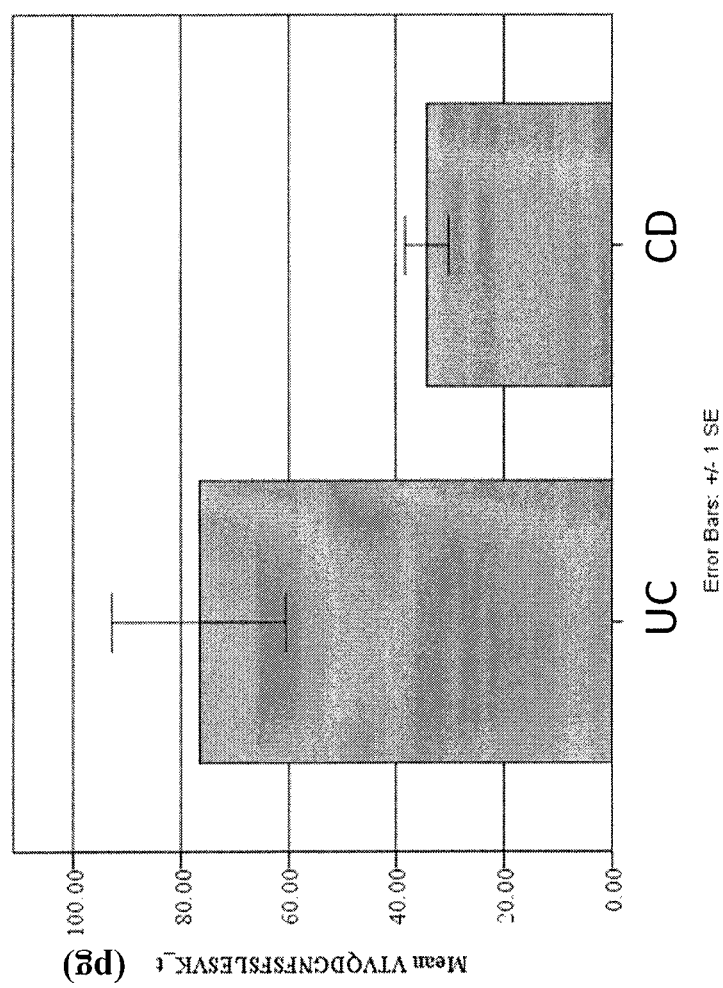
Figure 5:
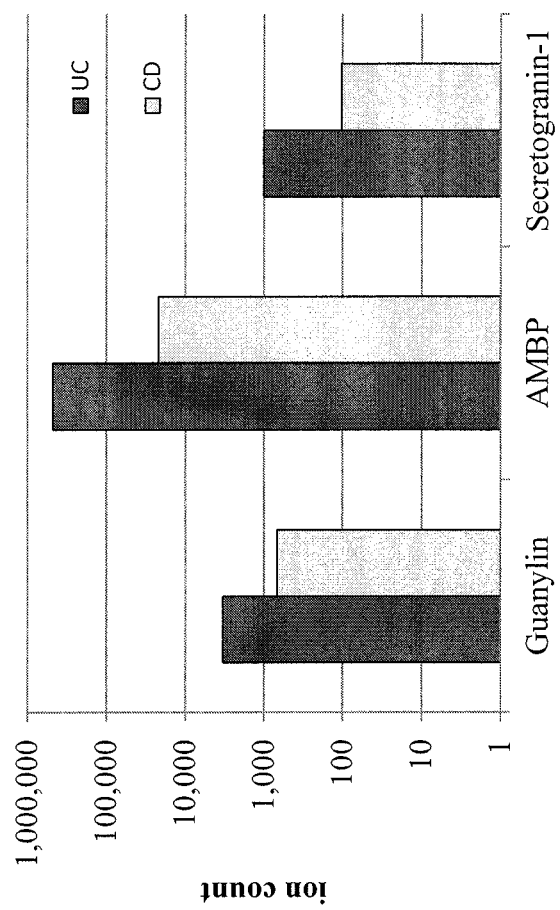
FIG. 5 is a graph showing the relative abundance of the peptides ADQTVLTEDEK (SEQ ID NO: 2), HHGPTITAK (SEQ ID NO: 11); and VTVQDGNFSFSLESVK (SEQ ID NO: 4), in pooled samples from subjects suffering from UC, or CD, as determined by ion count MS.

The relative abundance of peptides in samples from patients suffering from Ulcerative colitis (UC) and Crohn's disease (CD) as determined by absolute abundance using MRM is shown in FIGS. 4A, 4B and 4C, and as determined by relative abundance ion count MS is shown in FIG. 5.

As can be seen from FIGS. 4A to 4C and 5, the level of the peptides ADQTVLTEDK (SEQ ID NO: 2) from Secretogranin-1, HHGPTITAK (SEQ ID NO: 11) from AMBP, VTVQDGNFSFSLESV (SEQ ID NO: 4) from guanylin, are elevated in serum from patients suffering from Ulcerative colitis as compared to the level of the same peptides in patients suffering from Crohn's disease.

c. Peptides which Assess the Severity of IBD

Figure 11:
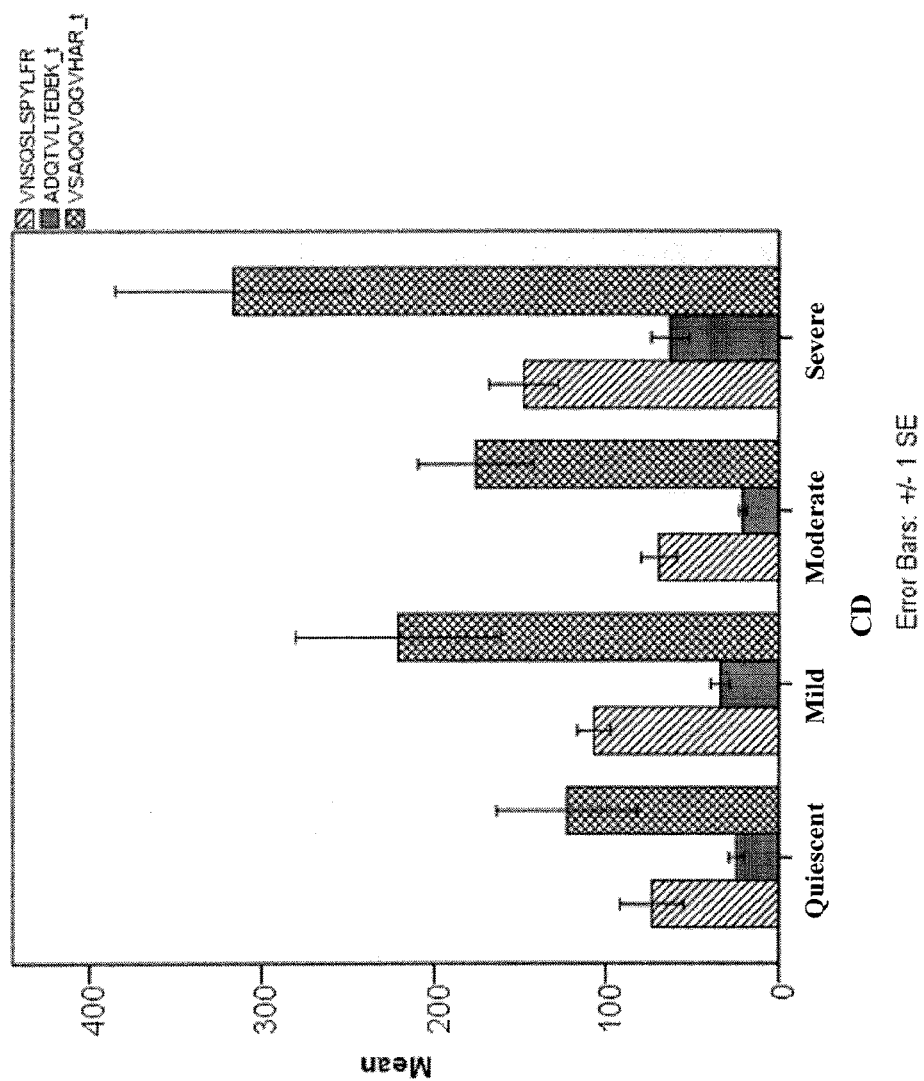
FIG. 11 shows the distribution of mean amounts (pg) of the peptides VNSQSLSPYLFR (SEQ ID NO: 7), VSAQQVQGVHAR (SEQ ID NO: 6) and ADQTVLTEDEK (SEQ ID NO: 2) following LC-MRM of enzyme digested serum samples from patients suffering from Crohn's disease in remission (Quiescent) and patients suffering from increasing severity of Crohn's disease (mild to severe).

The relative abundance of peptides in samples from patients: in remission from suffering from Crohn's disease (Qiescent); 1, suffering from mild Crohn's disease (mild); 2, Suffering from moderate Crohn's disease (moderate); or 3, suffering from severe Crohn's disease (severe), is shown in FIG. 11.

As can be seen from FIG. 11, the level of the peptides VSAQQVQGVHAR (SEQ ID NO: 6) from SPP 24, VNSQSLSPYLFR (SEQ ID NO: 7) from SPP 24 are elevated in serum from patients suffering from severe or active Crohn's disease as compared to the level of the same peptides in serum from patients in remission from suffering from Crohn's disease.

Figure 12:
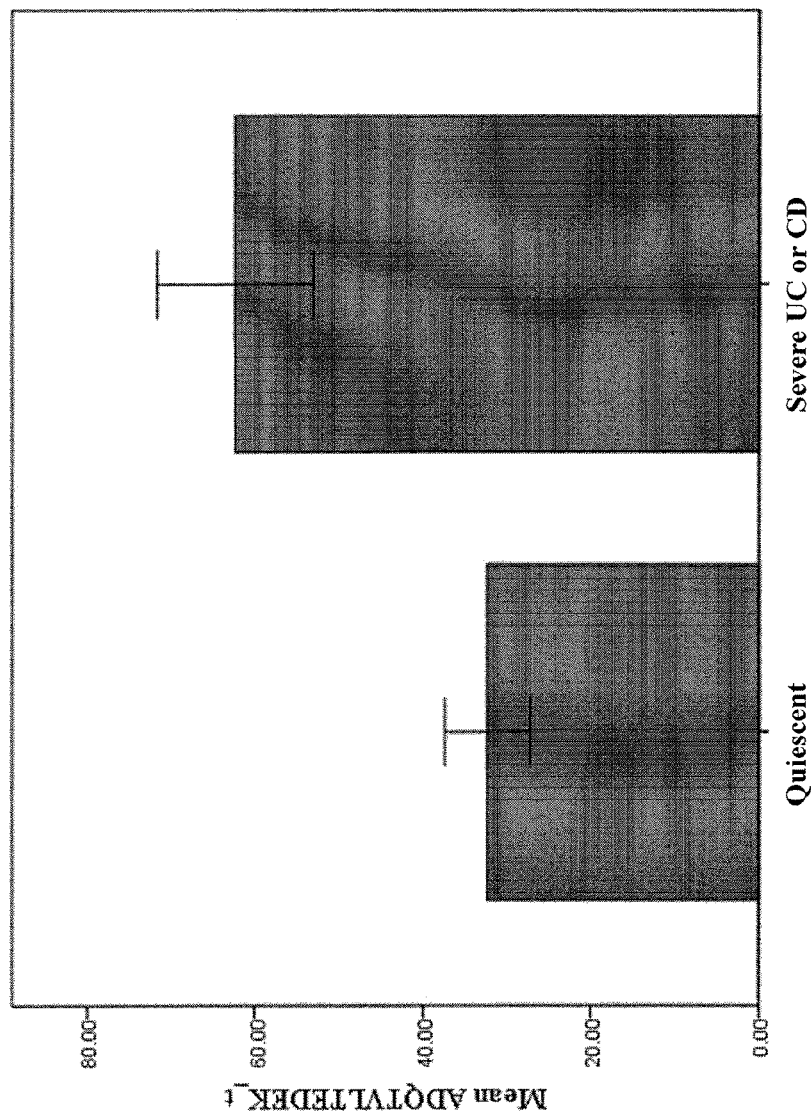
FIG. 12 shows the distribution of mean amounts of the peptide ADQTVLTEDEK (SEQ ID NO: 2) following MRM of enzyme digested serum samples from subjects suffering from IBD in remission (Quiescent), and severe UC or CD.

The relative abundance of the peptide in samples from patients: in remission from suffering from IBD (Qiescent); or suffering from severe UC or CD, is shown in FIG. 12. As can be seen from FIG. 12, ADQTVLTEDK (SEQ ID NO: 2) from Secretogranin-1 is elevated in subjects suffering from severe UC or CD.

Example 3

Assessment of Serum Using Reverse-Polynomial Dilution (RPD) Calibration in Multiple Reaction Monitoring (MRM) Plasma Assays RPD was used in conjunction with MRM to assess the levels of peptides in cohorts of UC and CD patients.

Light (crystalline powder) and stable isotope-labelled synthetic AQUA (heavy) peptides for SEQ ID NOS: 2, 4, 6, 7, 9 and 11 were obtained from Sigma-Aldrich (Missouri, USA) at greater than 95% purity. Isotopically labelled forms contained either a C-terminal $N^{15}$, $C^{13}$ on Arg, Lys or internal Leu. Peptides are shown in Table 3.

| Peptide | Name | SEQ ID NO |
|---|---|---|
| HHGPTITAK | AMBP | 11 |
| NLPSDSQDLGQHGLEED | Serglycine | 9 |
| VNSQSLSPYLFR | SPP24 | 7 |
| VSAQQVQGVHAR | SPP24 | 6 |
| ADQTVLTEDEK | Secretogranin-1 | 2 |
| VTVQDGNFSFSLESVK | Guanylin | 4 |

Amino acid residues in bold are those labelled with $C^{13}$, $N^{15}$.

All peptides were aliquoted into 1 nM amounts following amino acid analysis. Amino acid analysis was carried out at the Australian Proteome Analysis Facility with all peptides made up in stock amounts to 1 mg/ml with 50% acetonitrile, 5% acetic acid, 0.1% trifluoroactetic acid (TFA). Briefly, 20 µg amounts of synthetic peptides were reconstituted in 200 µl of 20% acetonitrile, 0.1% TFA, put into 10 µl aliquots and dried down. These samples were put through 24 hr gas phase hydrolysis with 6M HCl at 110° C. and analysed in duplicate using the Waters AccQTag Ultra chemistry on a Waters Acquity UPLC. The quantitative values were averaged and used for subsequent analysis.

Human plasma samples were obtained from Concord repatriation General Hospital, Sydney Australia. The collection of samples was approved by the Sydney Local Health District Human Research Ethics Committee (Approval Code: CH62/6/2011-154). Plasma samples were trypsin digested at a 100:1 protein to enzyme ratio, made up to 100 ml with 50mM NH4HCO3 (AMBIC) and incubated at 37° C. overnight. 5-1 of neat formic acid was used to terminate the digestion reaction, the samples dried, resuspended in 0.1% formic acid and desalted by 3 successive passes through C18 stage-tips (Thermo Fisher Scientific, MA, USA). Protein content was determined using the GE Healthcare 2-D Quant Kit (Uppsala, Sweden). The starting concentration of plasma used was 58 µg/µl and trypsin digested samples were reconstituted in 0.1% formic acid and aliquoted so that all experimental samples contained the same approximate final analysis of 0.1 µg/µl. RPD calibration was carried out with serial dilutions of 0.5, 1, 5, 25, 50 and 100 fmol of C13N15-labeled peptide that was normalised against the constant endogenous light target peptide signal from the plasma-digest background. RPD datapoints were fitted with a $2^{nd}$ order polynomial regression equation. All transitions were used for quantitation of each target peptide and the calibration standard was run in triplicate.

MRM transition lists consisting of 4-7 transitions per peptide precursor were developed in Skyline SRM Environment v1.4 (MacCoss lab, UW), and are show in Table 4 and refined by iterative experimentation and optimization using a 4000 Qtrap mas spectrometer (AB SCIEX, MA, USA) coupled to an ultimate 3000 HPLC and autosampler system (Dionex, Amsterdam, Netherlands). Samples were concentrated and desalted onto a micro C18 precolumn (500 µm×2 mm, Michrom Bioresources, USA) with $H_2O:CH_3CN$ (98:2, 0.05% v/v TFA) at 15 ml/minute. After 4 min washing the pre-column was automatically switched (Valco10 port valve, Houston, USA) into line with a fritless-nano column manufactured according to Gatlin et al. (1998) Anakl. Biochem. 263(1): 93-101. Peptides were eluted using a linear gradient of H2O:CH3CN (36:64, 0.1% (v/v)FA) at ~300 nL/min over 40 min. The pre-column was connected via a fused silica capillary (25 cm, 25 µm) to a low volume tee (Upchurch Scientific, USA) and introduced into the 4000 QTRAP mass spectrometer. Samples were analysed in positive ion mode with an ion spray voltage of 2.4 kV, curtain gas flow of 20 and nebulizing gas flow of 5. For MRM analysis, quadropoles were operated in unit resolution, and the dwell time was 66.2 ms. All samples were made to 10 µl and analysed in 1 µl injections. Raw.WIFF files were imported into Skyline SRM Environment for manual inspection and peak area-ratio calculation.

TABLE 4

| LC-ESI-MS/MS MRM method for peptides. | | | | | | | | | | |
|---|---|---|---|---|---|---|---|---|---|---|
| Peptide (SEQ ID NO:) | De-clustering Potential | Collision Energy | Rt(Min ± Window) | Q1 | | MRM Transitions (m/z) Q3 | | | | |
| 11 | 66.2 | 23.2 | 19.0 ± 1.0 | 481.26 | 824.46 | 687.40 | 630.38 | 533.33 | | |
| | | | | 485.27 | 832.48 | 695.42 | 638.40 | 541.34 | | |
| 9 | 98.7 | 48.6 | 29.2 ± 1.3 | 927.41 | 1240.54 | 1112.49 | 997.46 | 884.37 | | |
| | | | | 930.92 | 1247.56 | 1119.50 | 1004.48 | 891.39 | | |
| 7 | 82.6 | 36 | 35.4 ± 0.7 | 705.87 | 1197.63 | 1110.59 | 982.54 | 895.50 | 782.42 | 695.39 |
| | | | | 710.88 | 1207.63 | 1120.6 | 992.54 | 905.51 | 792.43 | 705.40 |
| 6 | 77.8 | 37.2 | 21.2 ± 0.6 | 640.35 | 1093.59 | 1022.55 | 894.49 | 766.43 | 667.36 | |
| | | | | 645.35 | 1103.59 | 1032.56 | 904.50 | 776.44 | 677.37 | |
| 2 | 76.7 | 31.3 | 23.5 ± 0.5 | 624.80 | 934.47 | 833.43 | 734.36 | 621.27 | | |
| | | | | 628.81 | 942.49 | 841.44 | 742.37 | 629.29 | | |
| 4 | 95.2 | 45.8 | 36.3 ± 2.5 | 878.94 | 1329.63 | 1214.60 | 1157.58 | 1043.54 | 896.47 | |
| | | | | 882.94 | 1337.64 | 1222.61 | 1165.59 | 1051.55 | 904.48 | |

The results of the analysis of the levels of the 6 peptides in groups of subjects suffering from IBD, UC, CD, in remission, or not suffering from any disease, are shown in FIGS. 6 to 11.

Figure 6:
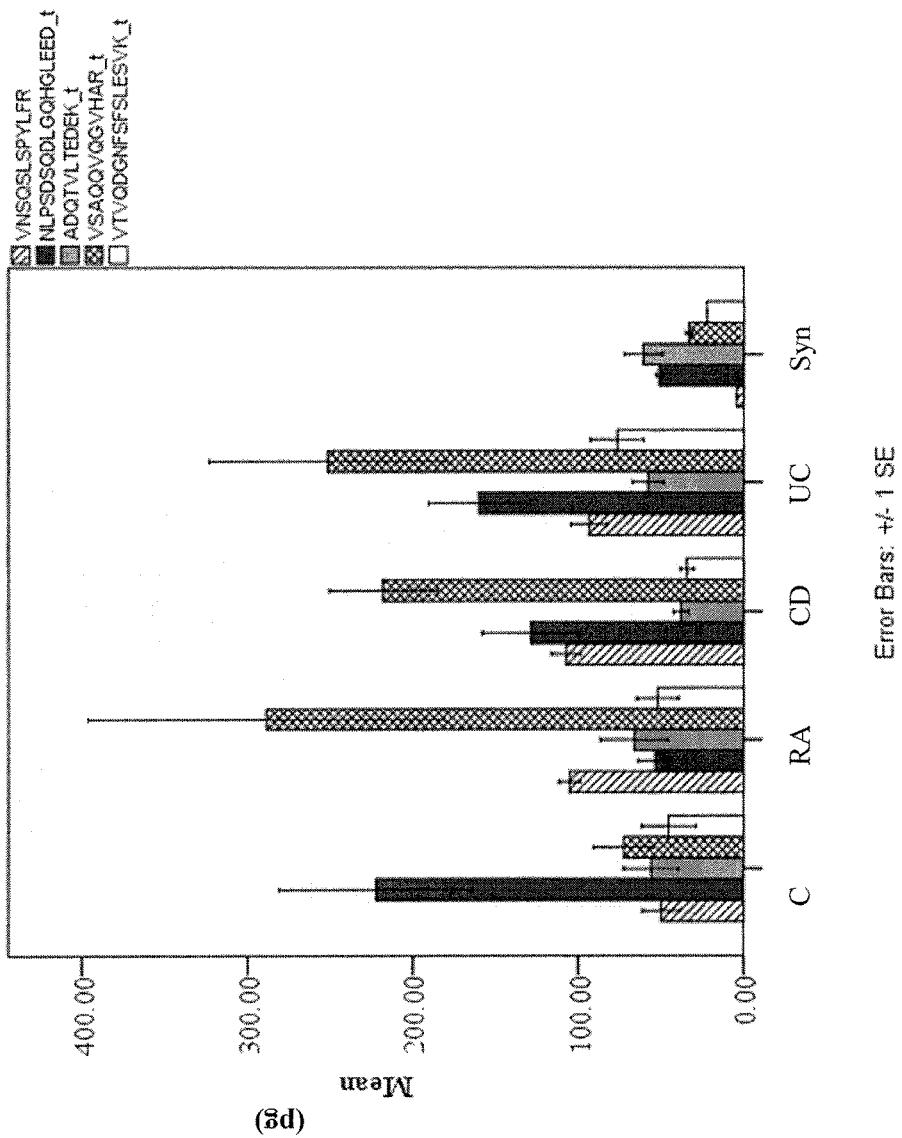
FIG. 6 is a graph showing the distribution of mean amounts (pg) of the peptides VNSQSLSPYLFR (SEQ ID NO: 7), NLPSDSQDLGQHGLEED (SEQ ID NO: 9), ADQTVLTEDEK (SEQ ID NO:2), VSAQQVQGVHAR (SEQ ID NO: 6) and VTVQDGNFSFSLESVK (SEQ ID NO: 4) following MRM of enzyme digested serum samples from: healthy patients (C); patients suffering from Rheumatoid arthritis (RA); patients suffering from Crohn's disease (CD); patients suffering from Ulcerative colitis (UC); and synovial fluid from an otherwise healthy patient suffering from inflamed synovium (Syn).

FIG. 6 shows the results of analysis of serum from subjects from the following groups: control (no disease) (0); subjects suffering from rheumatoid arthritis (1); subjects suffering from Crohn's disease (2); subjects suffering from Ulcerative colitis (3); and inflamed synovial fluid (4). As can be seen from FIG. 6, elevated levels of SEQ ID NO: 6, 7 distinguish between control and CD and UC, while elevated levels of SEQ ID NO: 4 distinguishes between the control and UC.

Figure 7:
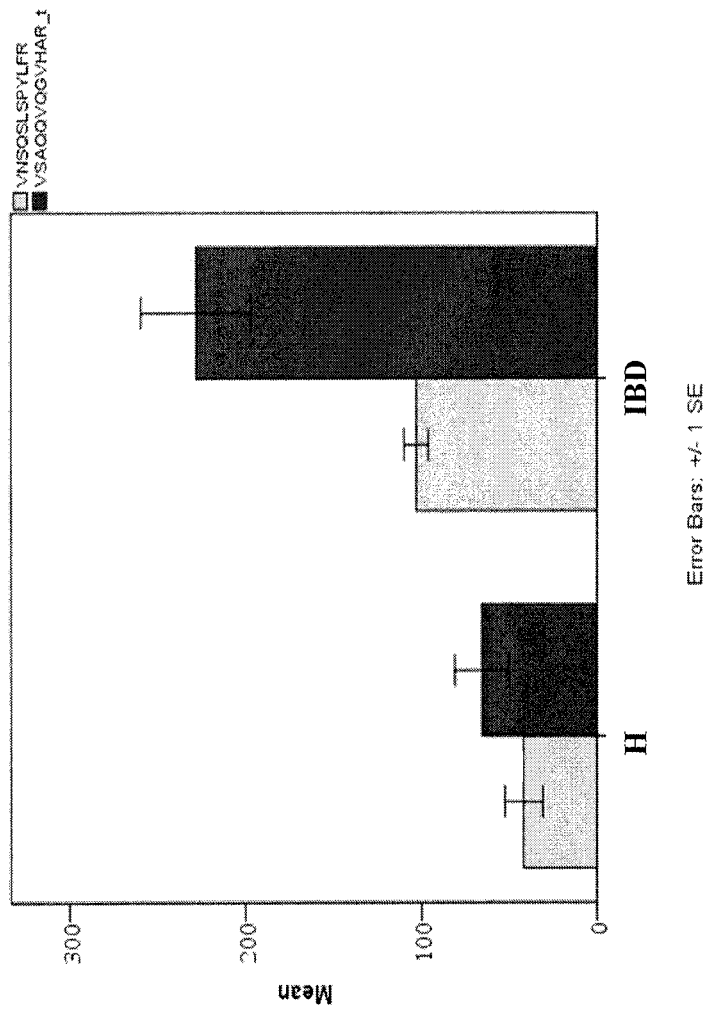
FIG. 7 shows the distribution of mean amounts (pg) of the peptides VNSQSLSPYLFR (SEQ ID NO: 7) and VSAQQVQGVHAR (SEQ ID NO: 6) following MRM of enzyme digested serum samples from: healthy patients (H); and patients suffering from IBD (IBD). ($p = <0.0002$ for both peptides).

FIG. 7 shows the levels of SEQ ID NO: 6 and 7 in subjects which either do not suffer from IBD (0) and subjects which do suffer from IBD (1). Both SEQ ID NO: 6 and 7 are elevated in serum of subjects suffering from IBD when compared to levels in subjects not suffering from IBD.

Figure 8:
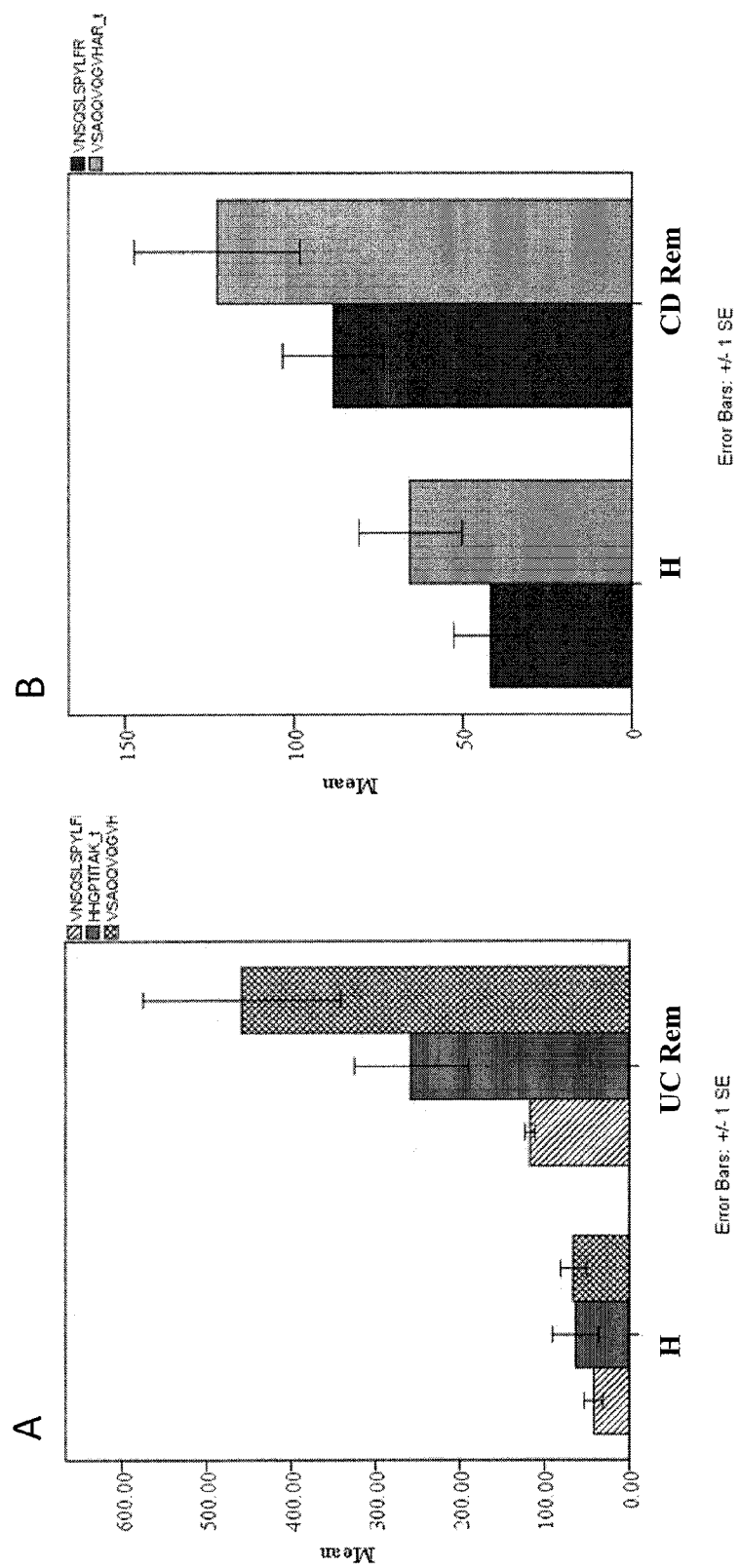
FIG. 8 shows the distribution of mean amounts (pg) of the peptides VNSQSLSPYLFR (SEQ ID NO: 7) ($p = 0.004$) and VSAQQVQGVHAR (SEQ ID NO: 6) ($p = 0.002$) and AMBP HHGPTITAK (SEQ ID NO: 11) ($p = 0.01$) following MRM of enzyme digested serum samples from A. healthy patients (H) and patients suffering from Ulcerative colitis in remission (UC Rem); and B. healthy patient (H) and patient suffering from Crohn's disease in remission (CDRem). ($p<0.002$ UC for both peptides, CD $p=VNS\ 0.017$, VSAQ $p=0.048$)
Figure 9:
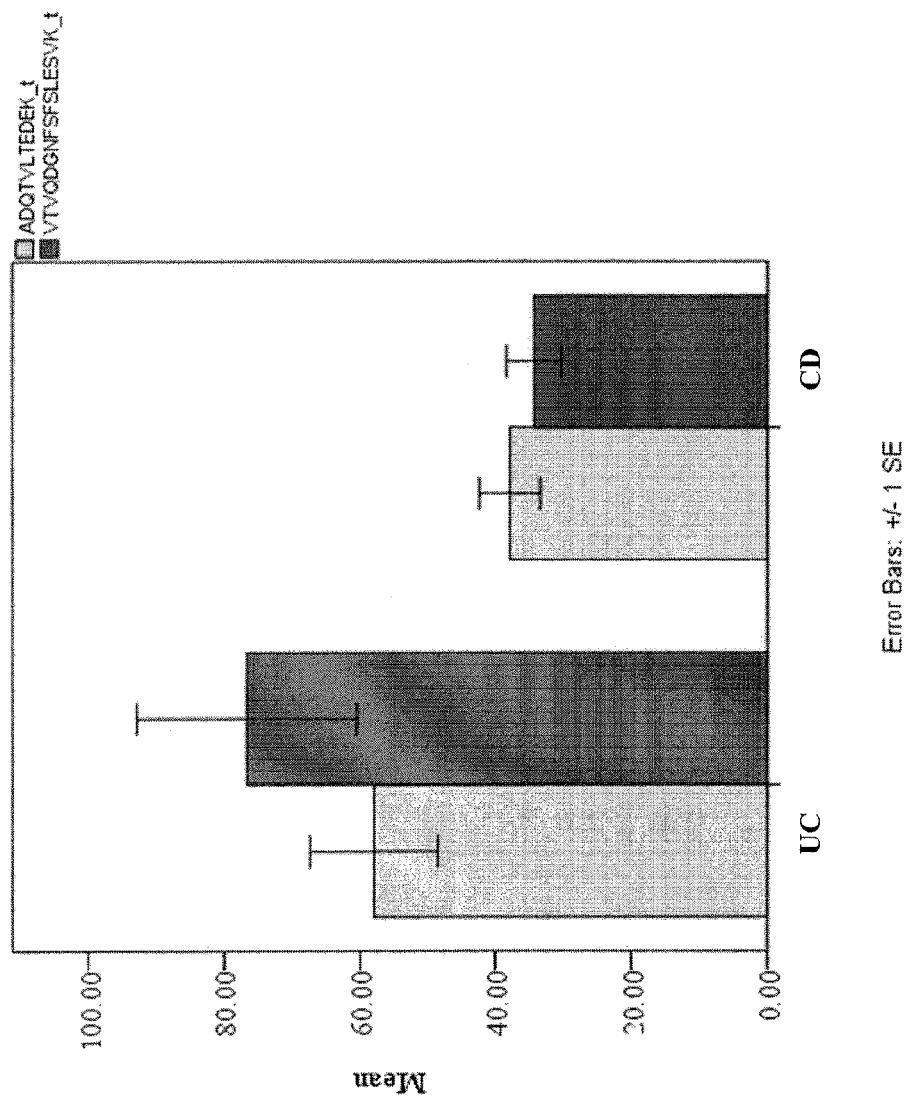
FIG. 9 shows the distribution of mean amounts (pg) of the peptide VTVQDGNFSFSLESVK (SEQ ID NO: 4) and ADQTVLTEDEK (SEQ ID NO: 2) following MRM of enzyme digested serum samples from patients suffering from Crohn's disease (CD) or Ulcerative colitis (UC).

FIG. 8 shows the distribution of mean amounts of peptides having SEQ ID NO: 6 and 7 from serum of subjects which are either: A: healthy (0) or suffering from UC in remission; or B. healthy (0) or suffering from CD in remission (1). Both SEQ ID NO: 6 and 7 are elevated in subjects suffering from UC in remission compared to healthy subjects. Similarly, SEQ ID NO: 6 and 7 are elevated in subjects suffering from CD in remission compared to healthy subjects. Accordingly, SEQ ID NOs 6 and 7 are capable of distinguishing between healthy subjects and those suffering from UC or CD in remission. FIG. 9 shows the levels of SEQ ID NO: 4 in subjects suffering from UC (0) and CD (1). Levels of SEQ ID NO: 4 are elevated in subjects suffering from UC relative to this subjects suffering from CD.

Figure 10:
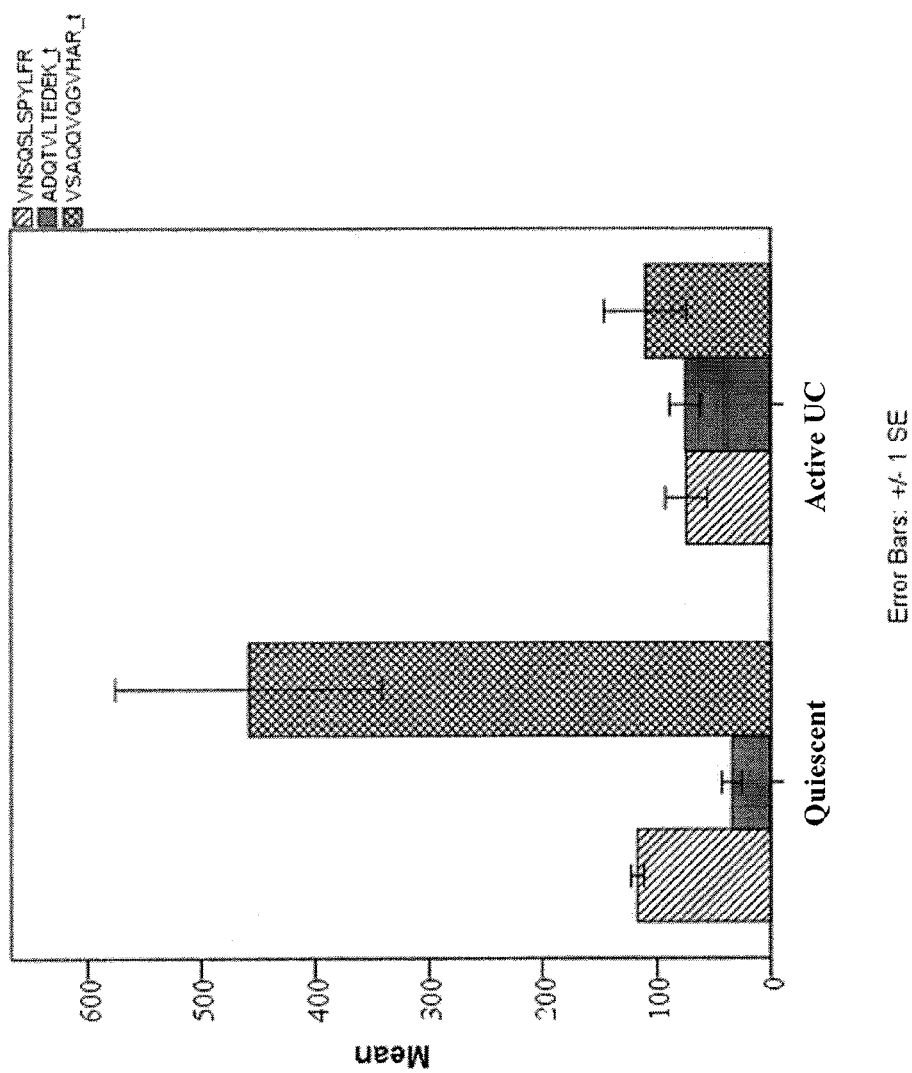
FIG. 10 shows the distribution of mean amounts (pg) of the peptides VNSQSLSPYLFR (SEQ ID NO: 7), VSAQQVQGVHAR (SEQ ID NO: 6) and ADQTVLTEDEK (SEQ ID NO: 2) following LC-MRM of enzyme digested serum samples from patients suffering from Ulcerative colitis in remission (Quiescent) or suffering from active Ulcerative colitis as determined by UC DAI score (ActiveUC).

FIG. 10 shows the level of peptides having SEQ ID NOs: 2, 6 and 7 in subjects suffering from UC in remission (0) and active UC (1). SEQ ID NO: 2 is reduced in serum of subjects suffering from UC in remission compared with subjects suffering from active UC. SEQ ID NO: 6 and 7 is elevated in serum of subjects suffering from UC in remission compared to the levels in subjects suffering from active UC.

FIG. 11 shows a comparison of the level of peptides having SEQ ID NOS: 2, 6 and 7 in subjects suffering from increasingly severe forms of CD (1 to 3). Levels of peptides having SEQ ID NOS: 2, 6 and 7 were elevated in subjects suffering from severe CD.

The correlation of peptides having SEQ ID NOs: 2, 4, 6 and 7 were assessed for with IBD, CD and UC were assessed for significance using a relative operating characteristic (ROC) analysis. The results of the ROC analysis are shown in Table 5.

TABLE 5

| | Condition | Peptides | AUC | probat |
|---|---|---|---|---|
| 1 | Peptides which distinguish between severe CD vs CD in remission | VSAQQVQGVHAR_t (SEQ ID NO: 6) | 0.75<br>0.8<br>0.833 | 0.068<br>0.028<br>0.015 |
| 2 | Peptides which distinguish between active IBD vs inactive IBD | ADQTVL TEDEK_t (SEQ ID NO: 2) | 0.867 | 0.045 |
| 3 | Peptides which distinguish between active IBD vs inactive IBD | VSAQQVQGVHAR_t (SEQ ID NO: 6) VNSQSLSPYLFR (SEQ ID NO: 7) | 0.833<br>0.900 | 0.068<br>0.028 |
| 4 | Peptide which distinguish between CD in remission vs Healthy subject | VSAQQVQGVHAR_t (SEQ ID NO: 6) VNSQSLSPYLFR (SEQ ID NO: 7) | 0.818<br>0.763 | 0.017<br>0.048 |
| 5 | Peptides which distinguish between UC in remission vs Healthy subject | VSAQQVQGVHAR_t (SEQ ID NO: 6) VNSQSLSPYLFR (SEQ ID NO: 7) | 0.964<br>1.000 | 0.004<br>0.002 |
| 6 | Peptides which distinguish between UC vs CD | VTVQDGNFSF SLESVK_t (SEQ ID NO: 6) | 0.778 | 0.006 |
| 7 | Peptides which distinguish between IBD vs Healthy subjects | VSAQQVQGVHAR_t (SEQ ID NO: 6) VNSQSLSPYLFR (SEQ ID NO: 7) | 0.852<br>0.865 | 0.0004<br>0.0002 |

A correlation analysis of the peptides was carried our using Spearmans Rho. The results are shown in Table 6.

TABLE 6

| Results of Spearman's Rho analysis | | | | | | | |
|---|---|---|---|---|---|---|---|
| | | SPP24 SEQ ID NO: 7 | SPP24 SEQ ID NO: 6 | AMBP SEQ ID NO: 11 | Serglycin SEQ ID NO: 9 | Secretogranin-1 SEQ ID NO: 2 | Guanylin SEQ ID NO: 4 |
| SPP24 SEQ ID NO: 7 | Correlation Coefficient | 1.000 | .574** | .405** | .036 | .217 | .431** |
| | Sig. (2-tailed) | .000 | .000 | .002 | .790 | .108 | .001 |
| | N | 56 | 56 | 56 | 56 | 56 | 56 |
| SPP24 SEQ ID NO: 6 | Correlation Coefficient | .574** | 1.000 | .688** | −.260 | −.131 | .181 |
| | Sig. (2-tailed) | .000 | . | .000 | .053 | .335 | .182 |
| | N | 56 | 56 | 56 | 56 | 56 | 56 |
| AMBP SEQ ID NO: 11 | Correlation Coefficient | .405** | .688** | 1.000 | −.327* | −.089 | .294* |
| | Sig. (2-tailed) | .002 | .000 | . | .014 | .512 | .028 |
| | N | 56 | 56 | 56 | 56 | 56 | 56 |

TABLE 6-continued

Results of Spearman's Rho analysis

|  |  | SPP24 SEQ ID NO: 7 | SPP24 SEQ ID NO: 6 | AMBP SEQ ID NO: 11 | Serglycin SEQ ID NO: 9 | Secretogranin-1 SEQ ID NO: 2 | Guanylin SEQ ID NO: 4 |
|---|---|---|---|---|---|---|---|
| Serglycin SEQ ID NO: 9 | Correlation Coefficient | .036 | −.260 | −.327* | 1.000 | .140 | .049 |
|  | Sig. (2-tailed) | .790 | .053 | .014 | . | .303 | .720 |
|  | N | 56 | 56 | 56 | 56 | 56 | 56 |
| Secretogranin-1 SEQ ID NO: 2 | Correlation Coefficient | .217 | −.131 | −.089 | .140 | 1.000 | .651** |
|  | Sig. (2-tailed) | .108 | .335 | .512 | .303 | .000 | .000 |
|  | N | 56 | 56 | 56 | 56 | 56 | 56 |
| Guanylin SEQ ID NO: 4 | Correlation Coefficient | .431** | .181 | .294* | .049 | .651** | 1.000 |
|  | Sig. (2-tailed) | .001 | .182 | .028 | .720 | .000 | .000 |
|  | N | 56 | 56 | 56 | 56 | 56 | 56 |

**Correlation is significant at the 0.01 level (2-tailed).
*Correlation is significant at the 0.05 level (2-tailed).

SUMMARY

Using RPD in conjunction with MRM on enzyme digests of serum samples:
  (a) peptides of segretogranin-1 and SPP24 are elevated in subjects suffering from severe CD relative to subjects in remission from CD;
  (b) peptides from SPP24 are elevated in subjects suffering from UC in remission compared to subjects suffering from active UC, and peptides from secretogranin-1 are reduced in subjects suffering from UC in remission compared to subjects suffering from active UC;
  (c) peptides from SPP24 are elevated in subjects suffering from UC and CD in remission when compared to healthy subjects (i.e. subjects not suffering from IBD);
  (d) peptides from Guanylin are elevated in subjects suffering from UC relative to subjects suffering from CD;
  (e) peptides from SPP24 are elevated in subjects suffering from IBD relative to healthy subjects (i.e. subjects not suffering from IBD).

The invention claimed is:

1. A method of diagnosing or assessing and treating an inflammatory bowel disease in a subject, comprising
   a. detecting the presence of one or more markers in the serum of the subject, wherein the one or more markers is selected from the group consisting of SPP24 or a fragment thereof and guanylin or a fragment thereof;
   b. comparing the level of the one or more markers in the serum of the subject relative to a reference value for the one or more markers;
   c. diagnosing the subject with IBD when the level of the one or more markers in the serum of the subject is elevated relative to the reference value; and
   d. treating the subject diagnosed with IBD with an anti-inflammatory agent, an immune modifier or an anti-TNF agent to the subject.

2. The method of claim 1, wherein the guanylin or a fragment thereof is a peptide comprising SEQ ID NO: 4.

3. The method of claim 1, wherein the SPP 24 or a fragment thereof is a peptide comprising SEQ ID NO: 6.

4. The method of claim 1, wherein the SPP 24 or a fragment thereof is a peptide comprising SEQ ID NO: 7.

5. The method of claim 1, wherein the one or more markers is guanylin or a fragment thereof, and the reference value is the level of the one or more markers in the serum of a subject not suffering from IBD, and wherein the subject is diagnosed with Ulcerative colitis when the level of guanylin or a fragment thereof is elevated relative to the reference value.

6. The method of claim 1, wherein the subject shows no or few symptoms of IBD, the one or more markers is SPP24 or a fragment thereof, and the reference value is the level of SPP24 or a fragment thereof in the serum of a subject not suffering from IBD, and wherein the subject is diagnosed with IBD in remission when the level of the SPP24 or a fragment thereof is elevated relative to the reference value.

7. The method of claim 1, wherein the reference value is the level of the one or more markers in the serum of a subject not suffering from IBD.

8. The method of claim 7, wherein the one or more markers is SPP 24 or a fragment thereof, and the reference value is the level of SPP 24 or a fragment thereof in the serum of a subject not suffering from IBD, wherein the subject is diagnosed with IBD when the level of SPP24 or a fragment thereof is elevated relative to the reference value.

9. The method of claim 1, wherein the one or more markers is SPP 24 or a fragment thereof.

10. The method of claim 1, wherein the reference value is the level of SPP24 or a fragment thereof in the serum of a subject suffering from active Ulcerative colitis, wherein the IBD the subject is diagnosed with is Ulcerative colitis in remission.

11. The method of claim 1, wherein the reference value is the level of SPP24 or a fragment thereof in the serum of a subject suffering from Crohn's Disease of a predetermined severity, wherein the IBD the subject is diagnosed with is Crohn's Disease of greater severity than the predetermined severity of the Crohn's Disease of the reference value.

* * * * *